United States Patent
Sista et al.

(10) Patent No.: US 10,379,112 B2
(45) Date of Patent: Aug. 13, 2019

(54) DROPLET ACTUATOR DEVICES AND METHODS EMPLOYING MAGNETIC BEADS

(71) Applicants: Advanced Liquid Logic, Inc., San Diego, CA (US); Duke University, Durham, NC (US)

(72) Inventors: Ramakrishna Sista, Cary, NC (US); Vamsee K. Pamula, Cary, NC (US); Michael G. Pollack, Durham, NC (US); Vijay Srinivasan, Cary, NC (US); Allen E. Eckhardt, San Diego, CA (US); Richard B. Fair, Durham, NC (US)

(73) Assignees: Advanced Liquid Logic, Inc., San Diego, CA (US); Duke University, Durham, NC (US)

( * ) Notice: Subject to any disclaimer, the term of this patent is extended or adjusted under 35 U.S.C. 154(b) by 266 days.

(21) Appl. No.: 14/719,731

(22) Filed: May 22, 2015

(65) Prior Publication Data
US 2015/0314293 A1    Nov. 5, 2015

Related U.S. Application Data

(63) Continuation of application No. 12/524,495, filed as application No. PCT/US2008/053545 on Feb. 11, 2008, now Pat. No. 9,046,514.
(Continued)

(51) Int. Cl.
*B01L 3/00* (2006.01)
*G01N 27/447* (2006.01)
(Continued)

(52) U.S. Cl.
CPC .... *G01N 33/54326* (2013.01); *B01L 3/50273* (2013.01); *B01L 3/502715* (2013.01);
(Continued)

(58) Field of Classification Search
CPC ......... B01L 3/502761; B01L 3/502715; B01L 2200/0647; B01L 2200/0673;
(Continued)

(56) References Cited

U.S. PATENT DOCUMENTS

| 4,127,460 A | 11/1978 | Gaske et al. |
| 4,244,693 A | 1/1981 | Guon |

(Continued)

FOREIGN PATENT DOCUMENTS

| EP | 0872949 A2 | 10/1998 |
| JP | 2001228149 A | 8/2001 |

(Continued)

OTHER PUBLICATIONS

Binks, "Wetting: theory and experiment", Current Opinion in Colloids and Interface Science, vol. 6, No. 1, 17-21, 2001.
(Continued)

*Primary Examiner* — Rebecca M Fritchman
(74) *Attorney, Agent, or Firm* — Illumina, Inc.

(57) ABSTRACT

A method of providing a droplet in contact with a magnetically responsive bead and having a reduced quantity of a substance. The method generally includes the steps of (a) providing a droplet actuator comprising: (i) a substrate comprising electrodes arranged for conducting droplet operations on a surface; (ii) a starting droplet comprising: (1) one or more magnetically responsive beads; (2) a starting quantity of the substance; and (3) a starting volume; (b) magnetically immobilizing the one or more magnetically responsive beads at a location which is at a distance from a target droplet splitting zone; (c) conducting one or more droplet operations comprising droplet dividing operations selected to divide the combined droplet to yield a set of droplets comprising: (i) a droplet comprising substantially all of the one or more magnetically responsive beads and
(Continued)

having a decreased quantity of the substance relative to the starting concentration; and (ii) a droplet substantially lacking the magnetically responsive beads.

18 Claims, 15 Drawing Sheets

Related U.S. Application Data

(60) Provisional application No. 60/900,653, filed on Feb. 9, 2007, provisional application No. 60/969,736, filed on Sep. 4, 2007, provisional application No. 60/980,772, filed on Oct. 17, 2007, provisional application No. 60/980,762, filed on Oct. 17, 2007.

(51) Int. Cl.
    *G01N 33/543*     (2006.01)
    *C12M 1/12*     (2006.01)
    *G01N 35/10*     (2006.01)
    *G01N 35/00*     (2006.01)

(52) U.S. Cl.
CPC ... *B01L 3/502761* (2013.01); *B01L 3/502784* (2013.01); *C12M 25/01* (2013.01); *C12M 25/16* (2013.01); *G01N 27/44717* (2013.01); *G01N 27/44786* (2013.01); *G01N 33/54386* (2013.01); *B01L 2200/025* (2013.01); *B01L 2200/028* (2013.01); *B01L 2200/0647* (2013.01); *B01L 2200/0673* (2013.01); *B01L 2200/141* (2013.01); *B01L 2300/0816* (2013.01); *B01L 2300/0864* (2013.01); *B01L 2300/0867* (2013.01); *B01L 2400/043* (2013.01); *B01L 2400/0427* (2013.01); *G01N 35/0098* (2013.01); *G01N 2035/1046* (2013.01)

(58) Field of Classification Search
CPC ....... B01L 2200/141; B01L 2300/0816; B01L 2300/0864; B01L 2300/0867; B01L 2400/0427; B01L 2400/043; B01L 2200/025; B01L 2200/028; B01L 3/50273; B01L 3/502784; G01N 35/0098; G01N 33/54326; G01N 33/54386; G01N 2035/1046; G01N 27/44786; G01N 27/44717; C12M 25/01; C12M 25/16
USPC .................... 435/79; 436/2; 422/67, 63, 400
See application file for complete search history.

(56) References Cited

U.S. PATENT DOCUMENTS

| | | | |
|---|---|---|---|
| 4,636,785 A | 1/1987 | Le Pesant |
| 5,038,852 A | 8/1991 | Johnson et al. |
| 5,176,203 A | 1/1993 | Larzul |
| 5,181,016 A | 1/1993 | Lee et al. |
| 5,225,332 A | 7/1993 | Weaver et al. |
| 5,240,994 A | 8/1993 | Brink et al. |
| 5,266,498 A | 11/1993 | Tarcha et al. |
| 5,370,842 A | 12/1994 | Miyazaki et al. |
| 5,455,008 A | 10/1995 | Earley et al. |
| 5,472,881 A | 12/1995 | Beebe et al. |
| 5,486,337 A | 1/1996 | Ohkawa et al. |
| 5,498,392 A | 3/1996 | Wilding et al. |
| 5,720,923 A | 2/1998 | Haff et al. |
| 5,779,977 A | 7/1998 | Haff et al. |
| 5,817,526 A | 10/1998 | Kinoshita et al. |
| 5,827,480 A | 10/1998 | Haff et al. |
| 5,945,281 A | 8/1999 | Prabhu et al. |
| 5,998,224 A | 12/1999 | Rohr et al. |
| 6,013,531 A | 1/2000 | Wang et al. |
| 6,033,880 A | 3/2000 | Haff et al. |
| 6,063,339 A | 5/2000 | Tisone et al. |
| 6,130,098 A | 10/2000 | Handique et al. |
| 6,152,181 A | 11/2000 | Wapner et al. |
| 6,180,372 B1 | 1/2001 | Franzen |
| 6,294,063 B1 | 9/2001 | Becker et al. |
| 6,319,668 B1 | 11/2001 | Nova et al. |
| 6,331,045 B1 | 12/2001 | Harvey |
| 6,432,290 B1 | 8/2002 | Harrison et al. |
| 6,453,928 B1 | 9/2002 | Kaplan et al. |
| 6,461,570 B2 | 10/2002 | Ishihara et al. |
| 6,485,913 B1 | 11/2002 | Becker et al. |
| 6,548,311 B1 | 4/2003 | Knoll |
| 6,565,727 B1 | 5/2003 | Shenderov |
| 6,591,852 B1 | 7/2003 | McNeely et al. |
| 6,596,238 B1 | 7/2003 | Belder et al. |
| 6,613,560 B1 | 9/2003 | Tso et al. |
| 6,632,655 B1 | 10/2003 | Mehta et al. |
| 6,673,533 B1 | 1/2004 | Wohlstadter et al. |
| 6,733,172 B2 | 5/2004 | Lee et al. |
| 6,734,436 B2 | 5/2004 | Faris et al. |
| 6,773,566 B2 | 8/2004 | Shenderov |
| 6,790,011 B1 | 9/2004 | Le Pesant et al. |
| 6,841,128 B2 | 1/2005 | Kambara et al. |
| 6,846,638 B2 | 1/2005 | Shipwash |
| 6,911,132 B2 | 6/2005 | Pamula et al. |
| 6,924,792 B1 | 8/2005 | Jessop |
| 6,955,881 B2 | 10/2005 | Tanaami |
| 6,958,132 B2 | 10/2005 | Chiou |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,163,612 B2 | 1/2007 | Sterling et al. |
| 7,189,359 B2 | 3/2007 | Yuan et al. |
| 7,211,223 B2 | 5/2007 | Fouillet et al. |
| 7,211,442 B2 | 5/2007 | Gilbert et al. |
| 7,251,392 B2 | 7/2007 | Kuiper et al. |
| 7,255,780 B2 | 8/2007 | Shenderov |
| 7,267,752 B2 | 9/2007 | King et al. |
| 7,310,080 B2 | 12/2007 | Jessop |
| 7,328,979 B2 | 2/2008 | Decre et al. |
| 7,329,545 B2 | 2/2008 | Pamuta et al. |
| 7,438,860 B2 | 10/2008 | Takagi et al. |
| 7,439,014 B2 | 10/2008 | Pamuta et al. |
| 7,454,988 B2 | 11/2008 | Tan |
| 7,458,661 B2 | 12/2008 | Kim et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,822,510 B2 | 10/2010 | Palk et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,093,062 B2 | 1/2012 | Winger et al. |
| 8,137,917 B2 | 3/2012 | Pollack et al. |
| 8,147,668 B2 | 4/2012 | Pollack et al. |

(56) References Cited

U.S. PATENT DOCUMENTS

| | | |
|---|---|---|
| 8,179,216 B2 | 5/2012 | Knospe |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0001544 A1 | 1/2002 | Hess |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0051971 A1 | 5/2002 | Stuelpnagel et al. |
| 2002/0058332 A1 | 5/2002 | Quake et al. |
| 2002/0143437 A1 | 10/2002 | Handique et al. |
| 2003/0007377 A1 | 1/2003 | Otaka |
| 2003/0007898 A1 | 1/2003 | Bohm et al. |
| 2003/0049177 A1 | 3/2003 | Smith et al. |
| 2003/0103021 A1 | 6/2003 | Young et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0041860 A1* | 3/2004 | Takahashi .............. B41J 25/308 347/8 |
| 2004/0055871 A1 | 3/2004 | Walton et al. |
| 2004/0055891 A1 | 3/2004 | Pamula et al. |
| 2004/0058450 A1 | 3/2004 | Pamula et al. |
| 2004/0086870 A1 | 5/2004 | Tyvoll et al. |
| 2004/0101445 A1 | 5/2004 | Shvets et al. |
| 2004/0180346 A1 | 9/2004 | Anderson et al. |
| 2004/0209376 A1 | 10/2004 | Natan et al. |
| 2004/0231987 A1 | 11/2004 | Sterling et al. |
| 2005/0036908 A1 | 2/2005 | Yu et al. |
| 2005/0056569 A1 | 3/2005 | Yuan et al. |
| 2005/0189049 A1 | 9/2005 | Ohno et al. |
| 2005/0227349 A1 | 10/2005 | Kim et al. |
| 2005/0260686 A1 | 11/2005 | Watkins et al. |
| 2005/0282224 A1 | 12/2005 | Fouillet et al. |
| 2006/0021875 A1 | 2/2006 | Griffith et al. |
| 2006/0039823 A1 | 2/2006 | Yamakawa et al. |
| 2006/0040375 A1 | 2/2006 | Amey et al. |
| 2006/0054503 A1 | 3/2006 | Pamula et al. |
| 2006/0102477 A1 | 5/2006 | Vann et al. |
| 2006/0164490 A1 | 7/2006 | Kim et al. |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1* | 11/2006 | Adachi ................ G01N 35/08 205/777 |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0075922 A1 | 5/2007 | Jessop |
| 2007/0178603 A1 | 8/2007 | Takii et al. |
| 2007/0179641 A1 | 8/2007 | Lucas et al. |
| 2007/0202538 A1 | 8/2007 | Glezer et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1* | 1/2008 | Paik et al. .................... 204/600 |
| 2008/0023330 A1 | 1/2008 | Viovy |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0166793 A1 | 6/2008 | Beer et al. |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamuta et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |

(56) References Cited

U.S. PATENT DOCUMENTS

| | | |
|---|---|---|
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0114490 A1 | 5/2011 | Pamula et al. |
| 2011/0118132 A1 | 5/2011 | Winger et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0303542 A1 | 12/2011 | Srinivasan et al. |
| 2012/0018306 A1 | 1/2012 | Srinivasan et al. |
| 2012/0132528 A1 | 5/2012 | Shenderov et al. |
| 2012/0165238 A1 | 6/2012 | Pamula et al. |
| 2013/0217583 A1 | 8/2013 | Link et al. |
| 2013/0280131 A1 | 10/2013 | Handique et al. |

FOREIGN PATENT DOCUMENTS

| | | |
|---|---|---|
| JP | 2005037346 | 2/2005 |
| JP | 2005130851 A | 5/2005 |
| JP | 2006078225 A | 3/2006 |
| JP | 2006276801 A | 10/2006 |
| JP | 2006317364 A | 11/2006 |
| JP | 2006329899 A | 12/2006 |
| JP | 2006329904 A | 12/2006 |
| JP | 2008096590 A | 4/2008 |
| JP | 2009534653 A | 9/2009 |
| WO | 9214138 A1 | 8/1992 |
| WO | 2000069565 A1 | 11/2000 |
| WO | 2000073655 A1 | 12/2000 |
| WO | 03045556 A2 | 6/2003 |
| WO | 2004011938 A2 | 2/2004 |
| WO | 2004029585 A1 | 4/2004 |
| WO | 2004030820 | 4/2004 |
| WO | 2004073863 A2 | 9/2004 |
| WO | 2005047696 A1 | 5/2005 |
| WO | 2005069015 A1 | 7/2005 |
| WO | 2006003292 A1 | 1/2006 |
| WO | 2006013303 A1 | 2/2006 |
| WO | 2006070162 A1 | 7/2006 |
| WO | 2006081558 | 8/2006 |
| WO | 2006085905 A1 | 8/2006 |
| WO | 2006124458 A2 | 11/2006 |
| WO | 2006127451 A2 | 11/2006 |
| WO | 2006129486 A1 | 12/2006 |
| WO | 2006132211 A1 | 12/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007073990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 A1 | 4/2009 |
| WO | 2009052348 A2 | 4/2009 |
| WO | 2009076414 | 6/2009 |
| WO | 2009086403 A2 | 7/2009 |

OTHER PUBLICATIONS

Chamberlain, et al., "Deletion screening of Duchenne musular dystrophy locus via multiplex DNA amplification", Nuc. Acid. Res. 16, pp. 11141-11156, 1988.

Cho, et al., "Concentration and binary separation of micro particles for droplet-based digital microfluidics", Lab Chip, vol. 7, 490-498, 2007.

Dorfman, et al., "Contamination-Free Continuouse Flow Microfluidic Polymerase Chain Reaction for Quantitative and Clinical Applications", Analytical Chemistry 77, 3700-3704, 2005.

Gijs, Mam, "Magnetic bead handling on-chip:new opportunities for analytical applications", Microfluidics and Nanofluidics, vol. 1, 22-40, Oct. 2, 2004.

Huang, et al., "MEMS-based sample preparation for molecular diagnostics", Analytical and Bioanalytical Chemistry, vol. 372, 49-65, 2002.

Jones, et al., "Dielectrophoretic liquid actuation and nanodroplet formation", J. Appl. Phys., vol. 89, No. 2, 1441-1448, Jan. 2001.

Margulies, et al., "Genome sequencing in microfabricated high-density picolitre reactors", Nature, vol. 437, 376-380 and Supplemental Materials, 2005.

Pinho, et al., "Haemopoietic progenitors in the adult mouse omentum: permanent production of B lymphocytes and monocytes", Cell Tissue Res., vol. 319, No. 1, 91-102, Jan. 2005.

Poliski, Making materials fit the future: accommodating relentless technological requirements means researchers must recreate and reconfigure materials, frequently challenging established laws of physics, while keeping an eye on Moore's Law, R&D Magazine Conference, Dec. 2001.

Russom, et al., "Pyrosequencing in a Microfluidic Flow-Through Device", Anal. Chem. vol. 77, 7505-7511, 2005.

Schwartz, et al., "Dielectrophoretic approaches to sample preparation and analysis", The University of Texas, Dissertation, Dec. 2001.

Tsuchiya, et al., "On-chip polymerase chain reaction microdevice employing a magnetic droplet-manipulation system", Sensors and Actuators B, vol. 130, 583-588, Oct. 18, 2007.

Wheeler, et al., "Electrowetting-Based Microfluidics for Analysis of Peptides and Proteins by Matrix-Assisted Laser Desportion/Ionization Mass Spectrometry", Anal. Chem. 76, 4833-4838, 2004.

Yi et al., "Microfluidics technology for manipulation and analysis of biological cells", Analytica Chimica Acta, vol. 560, 1-23, 2006.

Pamula et al., "Microfluidic electrowetting-based droplet mixing", Proceedings, MEMS Conference Berkeley, Aug. 24-26, 2001.

International Search Report dated Nov. 27, 2008 from PCT International Application No. PCT/US2008/053545.

International Preliminary Report on Patentability dated Aug. 11, 2009 from PCT International Application No. PCT/US2008/053545.

Office Action dated Oct. 31, 2014 from related U.S. Appl. No. 12/524,495.

Office Action dated Apr. 24, 2014 from related U.S. Appl. No. 12/524,495.

Office Action dated Aug. 7, 2012 from related U.S. Appl. No. 12/524,495.

Office Action dated May 3, 2012 from related U.S. Appl. No. 12/524,495.

Published Abstract from NIH Grant Project No. 1R43CA114993-01A2.

Published Abstract from NIH Grant Project No. 2R44DK066956-02.

(56) References Cited

OTHER PUBLICATIONS

U.S. Pat. No. 60,969,736, Sep. 4, 2007, Sista.
U.S. Pat. No. 60,957,717, Aug. 24, 2007, Allen.
Chakrabarty, "Automated Design of Microfluidics-Based Biochips: connecting Biochemistry of Electronics CAD", IEEE International Conference on Computer Design, San Jose, CA, Oct. 1-4, 2006, 93-100.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems , 1(3), Oct. 2005, 186-223.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Cotten et al., "Digital Microfluidics: a novel platform for multiplexed detection of lysosomal storage diseases", Abstract # 3747.9. Pediatric Academic Society Conference, 2008.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.
Mugele et al., "Electrowetting: from basics to applications", Institution of Physics Publishing, Journal of Physics: Condensed Matter, 2005, R705-R774.
Paik et al., "Adaptive Cooling of Integrated Circuits Using Digital Microfluidics", accepted for publication in IEEE Transactions on VLSI Systems, 2007, and Artech House, Norwood, MA, 2007.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Programmable flow-through real-time PCR using digital microfluidics", Proc. Micro Total Analysis Systems (µTAS), Handout, 2007.
Paik et al., "Programmable flow-through real-time PCR using digital microfluidics", Proc. Micro Total Analysis Systems (µTAS), Poster, 2007.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3., 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

(56) References Cited

OTHER PUBLICATIONS

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Sista, "Development of a Digital Microfluidic Lab-on-a-Chip for Automated Immunoassays with Magnetically Responsive Beads", PhD Thesis, Department of Chemical Engineering, Florida State University, 2007.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008.
Srinivasan et al., "Droplet-based microfluidic lab-on-a-chip for glucose detection", Analytica Chimica ACTA, vol. 507, No. 1, 2004, 145-150.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published online, May 2004, 3229-3235.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Weaver, "Application of Magnetic Microspheres for Pyrosequencing on a Digital Microfluidic Platform", Department of Electrical and Computer Engineering, Duke University, 2005.
Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.
Xu et al., "Automated Design of PIN-Constrained Digital Microfluidic Biochips Under Droplet-Interference Constraints", ACM Journal on Emerging Technologies is Computing Systems, vol. 3(3), 2007, 14:1-14:23.
Xu et al., "Automated solution preparation on a digital microfluidic lab-on-chip", PSI Bottlenecks Workshop, 2008.
Xu et al., "Automated, Accurate and Inexpensive Solution-Preparation on a Digital Microfluidic Biochip", Proc. IEEE Biomedical Circuits and Systems Conference (BioCAS), 2008, 301-304.
Xu et al., "Defect-Aware Synthesis of Droplet-Based Microfluidic Biochips", IEEE, 20th International Conference on VLSI Design, 2007.
Xu et al., "Digital Microfluidic Biochip Design for Protein Crystallization", IEEE-NIH Life Science Systems and Applications Workshop, LISA, Bethesda, MD, Nov. 8-9, 2007, 140-143.
Xu et al., "Droplet-Trace-Based Array Partitioning and a Pin Assignment Algorithm for the Automated Design of Digital Microfluidic Biochips", CODES, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yao et al., "Spot Cooling Using Thermoelectric Microcooler", Proc. 18th Int. Thermoelectric Conf. Baltimore, VA, pp. 256-259, Aug. 1999.

(56) References Cited

OTHER PUBLICATIONS

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16., Oct. 2006, 2053-2059.
Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Int'l , Conf. on Solid State Sensors. Actuators and Microsystems, Boston, Jun. 8-12, 2003, 1804-1807.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhao et al., "Droplet Manipulation and Microparticle Sampling on Perforated Microfilter Membranes", J. Micromech. Microeng., vol. 18, 2008, 1-11.
Zhao et al., "In-droplet particle separation by travelling wave dielectrophoresis (twDEP) and Ewod", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 3, 2006, 273-280.
Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.
Shikida et al., "Using wettability and interfacial tension to handle droplets of magnetic beads in a microchemical-analysis system", Sensors and Actuators B vol. 113: 563-569, Mar. 8, 2005.
Su et al. "Microfluidics-based Biochips: Technology Issues, Implementation Platforms, and Design Automation Challenges", IEEE Transactions on Computer Aided Design of Circuits and Systems, vol. 25, No. 2, pp. 211-223, Feb. 2006.
Pamula et al. (Co-Chair, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.
Cho et al., "Splitting a Liquid Droplet for Electrowetting-Based Microfluidics," Proceedings of 2001 ASME International Mechanical Engineering Congress and Exposition, IMECE2001/MEMS-23830, Nov. 11-16, 2001, New York, NY.
Brady, "Electrowetting for DNA Sequencing on CHIP," 2004 NNIN REU Research Accomplishments, pp. 26-27.
Fowler, "Lab-on-a-Chip Technology May Present New ESD Challenges", Electrostatic Discharge Journal, Mar. 2002.
Ding, "System level architectural optimization of semi-reconfigurable microfluidic system," M.S. Thesis, Duke University Dept of Electrical Engineering, 2000.
Fan, "Digital Microfluidics by Cross-Reference EWOD Actuation: Principle, Device, and System," PhD Dissertation, University of California Dept. of Mechanical Engineering, 2003.
Moon, "Electrowetting-on-dielectric microfluidics: Modeling, physics, and MALDI application," University of California, Los Angeles, 2005.
Lee et al., "Electrowetting and electrowetting-on-dielectric for microscale liquid handling," Sensors and Actuators A—Physical, vol. 95 (2-3): pp. 259-268, Jan. 1, 2002.
Moon et al., "Low voltage electrowetting-on-dielectric," Journal of Applied Physics, vol. 92 (7): pp. 4080-4087, Oct. 1, 2002.
Locascio et al. "Polymer microfluidic devices," Talanta, vol. 56, Feb. 2002, pp. 267-287.
Garrell et al., "Preventing Biomolecular Adsorption in Electrowetting-Based Biofluidic Chips," Analytical Chemistry, vol. 75, Oct. 2003, pp. 5097-5102.
Al-Rubeai et al., "The effect of Pluronic F-68 on hybridoma cells in continuous culture" , Applied Microbiology and Biology 1992. pp. 44-45.
Furdui et al., "Immunomagnetic T cell capture from blood for PCR analysis using microfluidic systems", Miniaturisation for Chemistry, Biology & Bioengineering, Lab Chip 2004, 4, 614-618.
Liu et al., "Effect of Non-Ionic Surfactants on the Formation of DNA/Emulsion Complexes and Emulsion-Medicated Gene Transfer", Pharmaceutical Research, pp. 1642-1646, vol. 13, No. 11, 1996.
Weber et al., "Specific Blood Purification by Means of Antibody-Conjugated Magnetic Microspheres", Centre for Biomedical Technology, Austria, Scientific and Clinical Applications of Magnetic Carriers, 1997.
Ybarra: "Independent Study and Undergraduate Research" [Online] Retrieved from the Internet: URL:http://www.ece.duke.edu/undergrads/independent.sub.--study.php.[retrieved on Jul. 24, 2008].

* cited by examiner

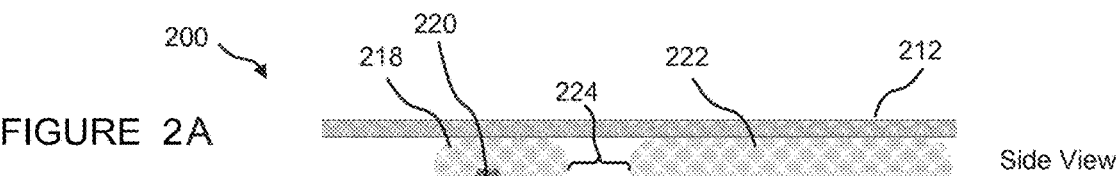
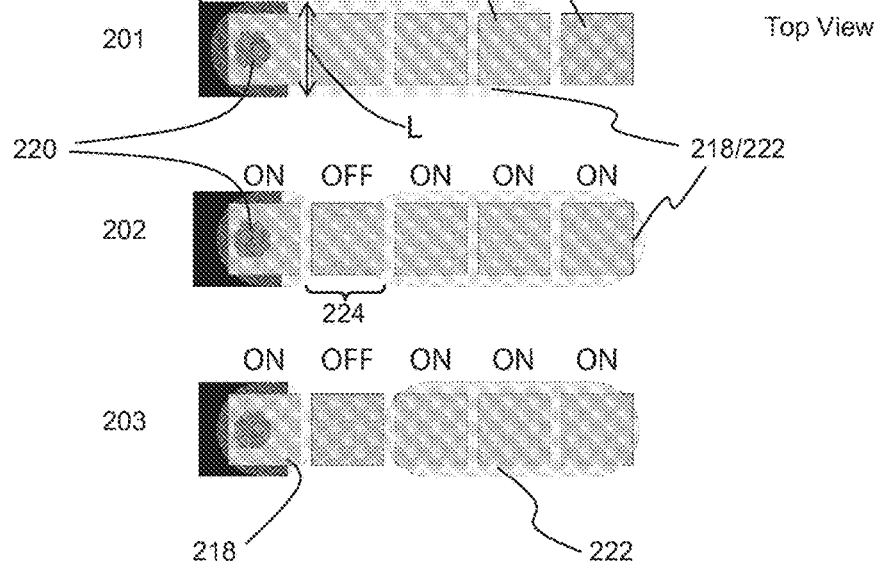

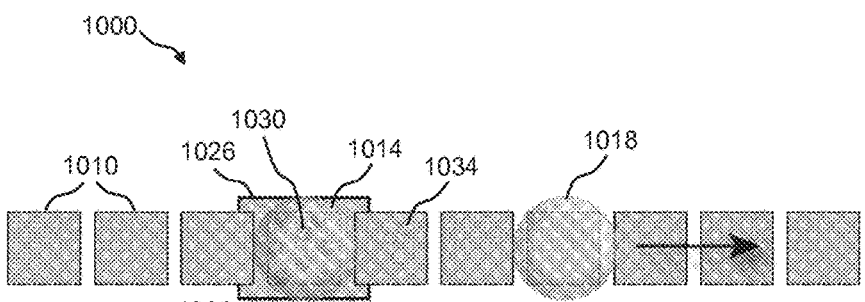
FIGURE 10 A
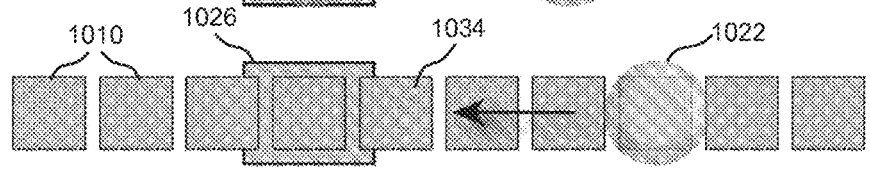
FIGURE 10 B
 Assay Droplet     Wash Droplet

DROPLET ACTUATOR DEVICES AND METHODS EMPLOYING MAGNETIC BEADS

RELATED APPLICATIONS

This application is a continuation of, claims priority to, and incorporates by reference U.S. patent application Ser. No. 12/524,495, filed on Jul. 24, 2009, entitled "Droplet Actuator Devices and Methods Employing Magnetic Beads," the application of which is a 371 National Entry of, claims priority to, and incorporates by reference International PCT Application No.: PCT/US2008/053545, with an international filing date of Feb. 11, 2008, entitled "Droplet Actuator Devices and Methods Employing Magnetic Beads", the application of which claims priority to and incorporates by reference related provisional U.S. Patent Application Nos.: 60/900,653, filed on Feb. 9, 2007, entitled "Immobilization of magnetically-responsive beads during droplet operations"; 60/980,772, filed on Oct. 17, 2007, entitled "Immobilization of magnetically-responsive beads in droplets"; 60/969,736, filed on Sep. 4, 2007, entitled "Droplet actuator assay improvements"; and 60/980,762, filed on Oct. 17, 2007, entitled "Droplet actuator assay improvements."

GRANT INFORMATION

This invention was made with government support under CA114993-01A2 and DK066956-02 awarded by the National Institutes of Health of the United States. The United States Government has certain rights in the invention.

FIELD OF THE INVENTION

The invention relates generally to the field of droplet actuators, and in particular, to droplet actuators configured for conducting droplet based protocols requiring droplet operations to be conducted using droplets comprising beads, especially magnetically responsive beads. The invention also relates to methods of making and using such droplet actuators.

BACKGROUND OF THE INVENTION

Droplet actuators are used to conduct a wide variety of droplet operations. A droplet actuator typically includes a substrate associated with electrodes for conducting droplet operations on a droplet operations surface thereof and may also include a second substrate arranged in a generally parallel fashion in relation to the droplet operations surface to form a gap in which droplet operations are effected. The gap is typically filled with a filler fluid that is immiscible with the fluid that is to be subjected to droplet operations on the droplet actuator.

In some applications of a droplet actuator there is a need for using "beads" for various assays. For protocols that make use of beads, the beads are typically used to bind to one or more target substances in a mixture of substances. The target substances may, for example, be analytes or contaminants. There is a need for an efficient approach to bead washing on a droplet actuator in order to reduce the amount of one or more substances in a bead-containing droplet that may be in contact with or exposed to the surface of the bead or beads.

BRIEF DESCRIPTION OF THE INVENTION

One aspect of the invention provides efficient immobilization of magnetically responsive beads for droplet operations that make use of magnetically responsive beads in droplet-based applications. Examples include assays that require execution of bead washing protocols, such as pyrosequencing and immunoassay applications. In one example, the invention provides techniques employing magnetic forces for immobilizing magnetically responsive beads during droplet splitting operations. The techniques of the invention are particularly useful in protocols for washing magnetically responsive beads within a droplet actuator. Among other advantages, the techniques of the invention avoid undue clumping or aggregation of the magnetically responsive beads. During droplet splitting operations, the techniques can usefully immobilize substantially all of the magnetically responsive beads within a droplet. Techniques of the invention may ensure immobilization and retention of substantially all magnetically responsive beads during a droplet washing operation. Upon completion of a washing process, the techniques of the invention ensure resuspension of substantially all of the magnetically responsive beads within the liquid and with substantially no clumping or aggregation thereof.

Another aspect of the invention provides improved droplet actuators and related methods for effecting improved droplet-based assay operations. Embodiments of the invention provide mechanisms for reducing the crossover of magnetic fields within a droplet actuator. Other embodiments of the invention provide mechanisms for reducing the carryover of beads and other substances within a droplet actuator. Yet other embodiments of the invention provide mechanisms for improving droplet detection operations within a droplet actuator.

Definitions

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay regent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads.

The beads may include one or more populations of biological cells adhered thereto. In some cases, the biological cells are a substantially pure population. In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, avoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into tow or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

When a given component, such as a layer, region or substrate, is referred to herein as being disposed or formed "on" another component, that given component can be directly on the other component or, alternatively, intervening components (for example, one or more coating, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates, using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

BRIEF DESCRIPTION OF THE DRAWINGS

FIGS. 2A and 2B illustrate a side and top views of a section of a droplet actuator that includes a magnet that is place at a position which is array from the splitting zone;

FIGS. 10A and 10B illustrate a top view of a section of a droplet actuator configured to reduce carryover;

DETAILED DESCRIPTION OF THE INVENTION

The present invention relates, among other things, to droplet actuators configured for immobilizing magnetically-responsive beads and to methods of making and using such droplet actuators. As an example, the droplet actuators are useful for immobilizing beads in droplets on the droplet actuators, thereby facilitating the execution of protocols which require immobilization of such beads, sued as bead washing protocols. The invention also provides techniques for reducing or eliminating carryover of substances from droplet to droplet in a droplet actuator and techniques for maximizing signal detection on a droplet actuator.

8.1 Bead Loss During Droplet Splitting

Figure 1A:
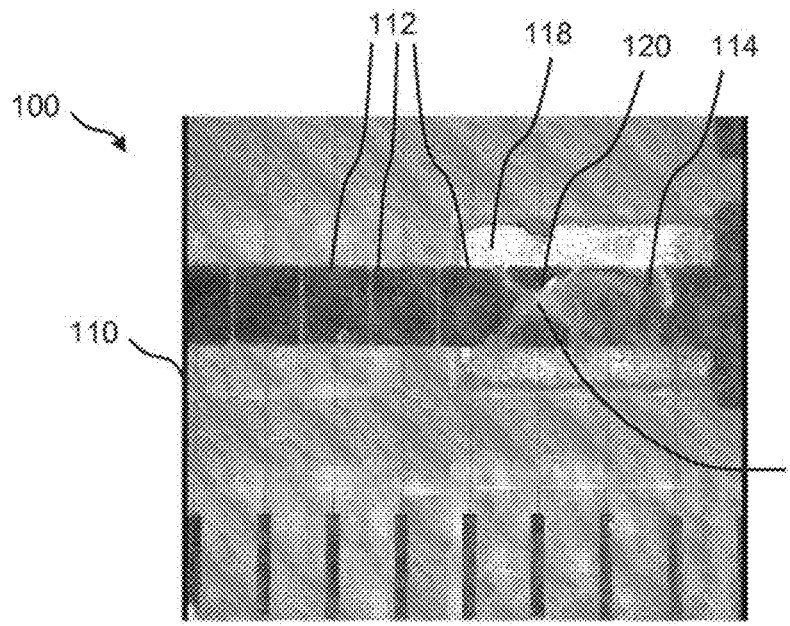
FIGS. 1A and 1B illustrate first and second top views, respectively, of a portion of a droplet actuator in use during a first and second phase, respectively, of a droplet splitting operation.
Figure 1B:
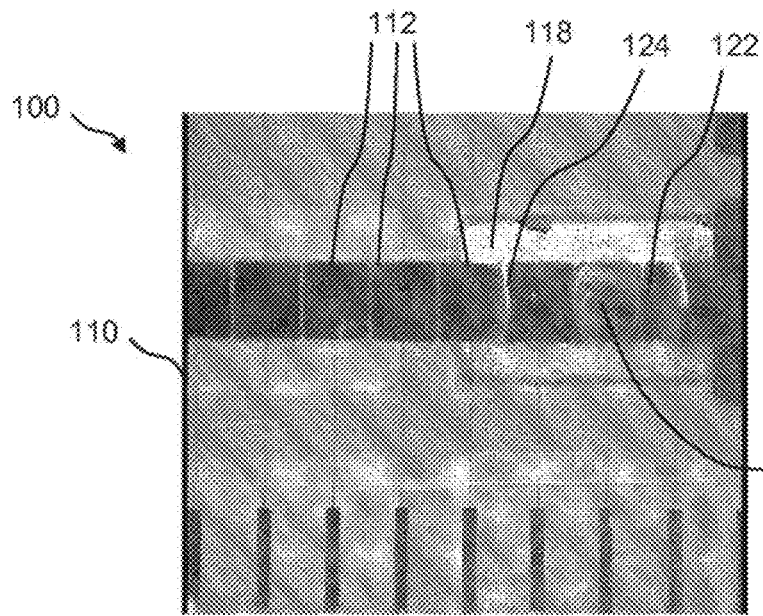

FIGS. 1A and 1B illustrate first and second top views, respectively, of a droplet actuator 100 in use during a first and second phase, respectively, of a droplet splitting operation. Droplet actuator 100 makes use of an arrangement that is not suitably arranged for efficiently splitting a droplet using the specific technique shown without loss of magnetically responsive beads. Droplet actuator 100 includes a first substrate 110 and a second substrate (not shown) arranged with a gap therebetween, which serves as a fluid path. First substrate 110 includes a set of droplet operation electrodes 112 configured for conducting droplet operations on slug-shaped droplet 114, which is suspended in a filler fluid and includes magnetically responsive beads 116. A magnet 118 may be arranged in sufficient proximity to droplet operation electrodes 112 to permit some degree of immobilization of the magnetically responsive beads 116.

FIGS. 1A and 1B show a splitting operation that is taking place in the presence of a magnetic field produced within droplet actuator 100 by magnet 118. The placement of magnet 118 is not suitable for localizing substantially all of magnetically responsive beads 116 in a centralized location (e.g., away from the edges of the droplet) within the portion of droplet 114 that is selected to retain the beads after the splitting operation. Consequently, a certain quantity of magnetically responsive beads 116 bridge splitting zone 120 during the droplet splitting operation, as shown in FIG. 1A, and a loss of beads results, as shown in FIG. 1B. FIG. 1B shows a first droplet 122 that contains a certain quantity of the original quantity of magnetically responsive beads 116 and a second droplet 124 that contains a certain remaining quantity of the original quantity of magnetically responsive beads 116. In other words, the end result of the illustrated splitting operation is a loss of magnetically responsive beads 116. The inventors have discovered that a contributing factor to the loss of beads is that a full quantity of magnetically responsive beads 116 is not suitably attracted, immobilized, and retained at a centralized location within droplet 114 and/or at a sufficient distance from splitting zone 120.

8.2 Magnet Configurations for Preventing/Reducing Bead Loss

Among other things, the invention provides improved droplet actuators that have various magnet configurations in which magnets are arranged for efficiently splitting bead-containing droplets and washing magnetically responsive beads are described with reference to FIGS. 2, 3, 4, 5A, and 5B. These figures illustrate nonlimiting examples of magnet configurations in combination with a droplet actuator splitting droplets with little or no bead loss, and are, among other things, useful for efficiently washing magnetically responsive beads. One or more magnets may be arranged in proximity to a droplet on a droplet actuator such that magnetically responsive beads are suitably attracted and immobilized within the droplet, preferably at a centralized location away from the neck that forms during splitting operations. In this approach, all or substantially all magnetically responsive beads are retained within a single droplet upon completion of a droplet splitting operation. Similarly, the spitting operation may be performed in a droplet slug which is at a distance from the immobilized beads which is sufficient to reduce or eliminate bead loss. As will be explained with respect to the examples below, one or more magnets may be arranged with respect to the droplet actuator structure above, below, and/or beside, the magnetically-responsive bead-containing droplet and any combinations thereof to achieve this purpose.

8.2.1 Position of Magnet Relative to Splitting Zone

FIGS. 2A and 2B illustrate side and top views of a droplet actuator 200. In this embodiment, the magnet is placed at a position which is sufficiently distant from the portion of the droplet which is breaking during the splitting operation, splitting zone 224 (or vice versa, the splitting zone may be said to be placed at sufficient distance from the magnet position), to reduce or eliminate bead loss during a droplet splitting operation. Further, the magnet is positioned so that the beads are generally centrally located along a lateral diameter L of the droplet (top view). Droplet actuator 200 includes a first substrate 210 and a second substrate 212 separated to province a gap for conducting droplet operations, though only one substrate is required. A set of droplet operation electrodes 214 is associated with one or both of the substrates and arranged for conducting one or more droplet operations. Droplet actuator 200 may include a magnet 216 that is arranged in sufficient proximity to droplet 218/222 to substantially immobilize magnetically responsive beads 220 during a droplet splitting operation. For example, the magnet may be arranged as a component of the droplet actuator and/or in sufficient proximity to the droplet actuator to immobilize the magnetically responsive beads in droplet 218/222 in the gap. Droplet 218/222 may be surrounded by a filler fluid (not shown). Droplet 218/222 contains a quantity of magnetically responsive beads 220 immobilized by magnet 216.

Magnet 216 is positioned relative to one or more droplet operation electrodes 214, in order to localize beads 220 in a region of the portion of the droplet 218/222 that is to form droplet 218 without permitting substantial loss of beads 218 during the droplet splitting operation to droplet 222.

In operation, a splitting operation is achieved without substantial loss of magnetic beads 220 by: as shown in 201, providing a droplet actuator 200 with electrodes activated (ON) to form combined droplet 218/222 and magnet 216 is arranged in a position which causes substantially all of magnetically responsive beads 220 to be attracted to magnet 216 in a zone of droplet 218/222 that prevents substantial loss of magnetically responsive beads 220 to droplet 222. Magnet 216 may be arranged so that magnetically responsive beads 220 attracted thereto are localized at a generally centralized location along lateral diameter L within combined droplet 218/222 and away from the droplet split zone 224. During a droplet splitting operation as shown in 202, an intermediate electrode is deactivated (OFF) to cause splitting at split zone 224. Substantially all magnetically responsive beads 220 are retained in droplet 218, and droplet 222 is formed and is substantially free of magnetically responsive beads 220, as shown in 203.

A process for washing magnetically responsive beads 20 may, in one embodiment, involve the repetition of droplet merging (with a wash droplet), bead immobilization, splitting, and bead resuspension operations until acceptable levels of washing are achieved.

8.2.2 Two-Magnet Arrangement to Produce Bead Column

Figure 3:
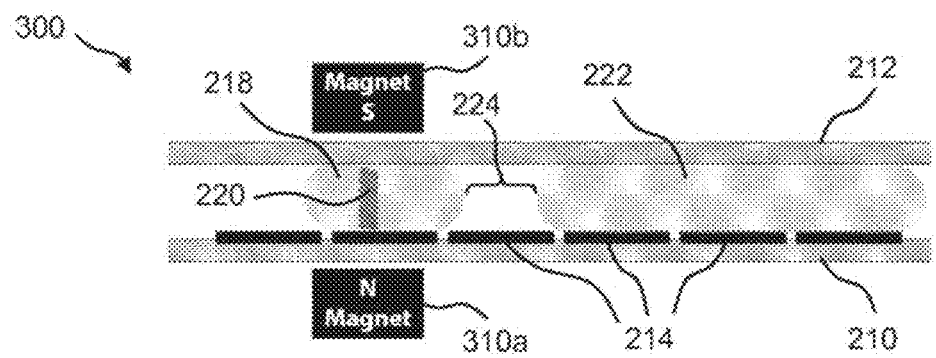
FIG. 3 illustrates a side view of a section of a droplet actuator that includes two magnets that are arranged above and below droplet.

FIG. 3 illustrates a side view of a droplet actuator 300. Droplet actuator 300 is generally configured as described is FIG. 2, except that it includes two magnets, magnet 310*a* and 310*b*, arranged below and above droplet 218. The magnets may be integral with droplet actuator 300 and/or arranged in close proximity to the outer side of first substrate 210 and second substrate 212. In general, the magnets 310*a* and 310*b* may be arranged such that opposite poles are facing one another. In one example, the north or positive pole of magnet 310*a* is facing the south or negative pole of magnet 310*b*, as shown in FIG. 3.

Magnets 310*a* and 310*b* may be separate magnets or, alternatively, magnets 310*a* and 310*b* may be opposite poles of a single U-shaped, C-shaped, or horseshoe-shaped permanent magnet or electromagnet. The arrangement of magnets 310*a* and 310*b* may cause magnetically responsive beads 220 to be immobilized and retained in a column-shaped duster. The magnets are preferably arranged to localize beads within droplet 218 in a position which is away form splitting zone 224 in the portion of the combined droplet (not shown) in which the beads are to be retained. Further, the magnets are preferably aligned to centrally localize the beads along lateral diameter L within the combined droplet (not shown).

8.2.3 Multiple Magnet Pairs to Centralize Beads

Figure 4A:
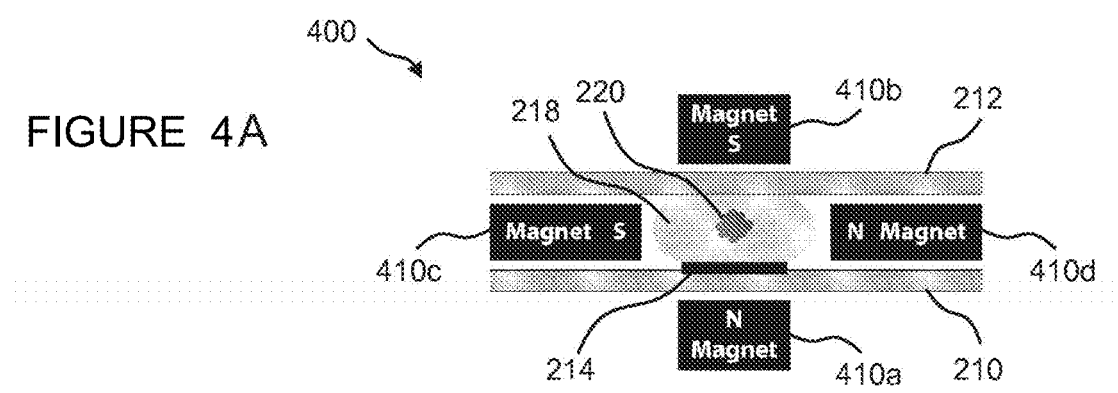
FIGS. 4A and 4B illustrate side views of a section of a droplet actuator that includes four magnets that arranged at positions surrounding the droplet.
Figure 4B:
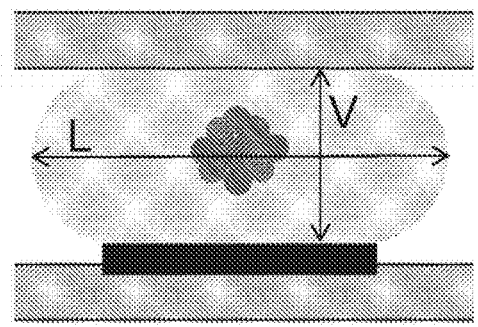

FIGS. 4A and 4B illustrate side views of a droplet actuator 400. Droplet actuator 400 is generally configured like droplet actuator 200 described in FIG. 2, except that it includes four magnets arranged at positions surrounding the droplet. In general, the arrangement illustrates the embodiment in which multiple magnet pairs with positive/negative poles facing each other are arranged to generally centrally locate beads 220 in the combined droplet prior to splitting. As illustrated in FIG. 4B, the beads are generally centrally located along a vertical dimension V and a lateral dimension L. In the example illustrated, droplet actuator 400 includes four magnets, such as a magnet 410*a*, 410*b*, 410*c*, and 410*d*.

Magnets 410*a* and 410*b* may be arranged in close proximity to the droplet, equally spaced on either side of the droplet, with opposite poles facing each other. For example, the north pole of magnet 410*a* may face the south pole of magnet 410*b*. Magnets 410*c* and 410*d* may be arranged in close proximity to the droplet, equally spaced on either side of the droplet, with opposite poles facing each other. For example, the north pole of magnet 410*d* may face the south pole of magnet 410*c*. Magnet pair 410*a*/410*b* may generally be aligned at right angles around the droplet relative to magnet pair 410*c*/410*d*. In the illustrated embodiment, magnet pair 410*a*/410*b* has a vertical orientation around the droplet, and magnet pair 410*c*/410*d* has a horizontal orientation around the droplet. Any orientation around the droplet achieving the generally central localization of beads along lateral dimension L and vertical dimension V will suffice to achieve the desired central immobilization.

Magnets 410*a* and 410*b* may be arranged in close proximity to the outer side of first substrate 210 and second substrate 212, respectively, such that the magnetic field of magnets 410*a* and 410*b* may pass through the gap between first substrate 210 and second substrate 212 of droplet actuator 400. Magnets 410*a* and 410*b* are arranged such that opposite poles are facing one another. In one example, the north pole of magnet 410*a* is facing the south pole of magnet 410*b*, as shown in FIG. 4. Similarly, magnets 410*c* and 410*d* are arranged in close proximity to a first side and a second side, respectively, of droplet actuator 400, such that the magnetic field of magnets 410*c* and 410*d* may pass through the gap of droplet actuator 400 and perpendicular to the magnetic field of magnets 410*a* and 410*b*. Magnets 410*c* and 410*d* are arranged such that opposite poles are facing one another. In one example, the north pole of magnet 410*d* is facing the south pole of magnet 410*c*, as shown in FIG. 4.

Magnets 410*a* and 410*b* may be separate magnets or, alternatively, magnets 410*a* and 410*b* may be opposite poles of a single U-shaped, C-shaped, or horseshoe-shaped permanent magnet or electromagnet. Similarly, magnets 410*c* and 410*d* may be separate magnets or, alternatively, magnets 410*c* and 410*d* may be opposite poles of a single U-shaped, C-shaped, or horseshoe-shaped permanent magnet or electromagnet. Because the magnetic field of magnets 410*a* and 410*b* and magnets 410*c* and 410*d*, respectively, intersect at the center of the fluid path within droplet actuator 400, the magnetically responsive beads 220 are magnetically immobilized and retained in a cluster that is centralized within the combined droplet and retained in droplet 218 following the splitting operation.

8.2.4 Illustration of Splitting with Substantially No Bead Loss

Figure 5A:
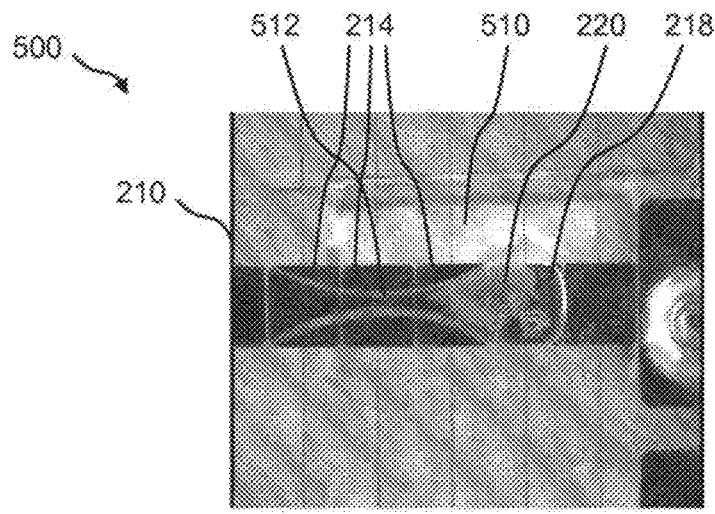
FIGS. 5A and 5B illustrate a first and second top view, respectively, of a section of a droplet actuator during a first and second phase, respectively, of a droplet splitting operation.
Figure 5B:
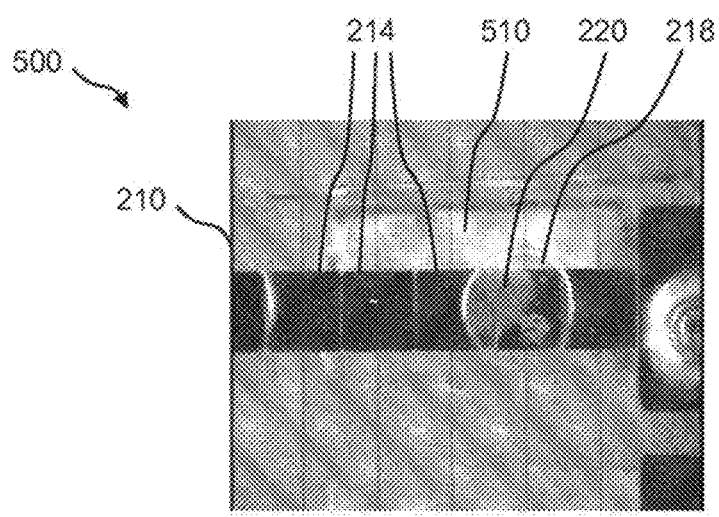

FIGS. 5A and 5B illustrate a first and second top view, respectively, of a droplet actuator 500 during a first and second phase, respectively, of a droplet splitting operation. Droplet actuator 500 may alternatively be configured like any of the example droplet actuators 200, 300, and 400. Droplet actuator 500 of FIGS. 5A and 5B makes use of magnet forces that are suitably arranged for use in a splitting operation designed to result in substantially complete retention of beads in a single droplet, such as a process for washing magnetically responsive beads.

In particular, FIGS. 5A and 5B show a splitting operation that is taking place at a sufficient distance from localized beads 220 to permit a splitting operation that results in substantially complete retention of magnetically responsive beads in droplet 218 and a droplet that is substantially free of magnetically responsive beads. The position of magnet face 510 is suitably arranged to magnetically immobilize substantially all of magnetically responsive beds 220 at a centralized location within the droplet and at a distance from the splitting zone that is sufficient to achieve the desired retention of magnetically responsive beads 220 in droplet 218. As a result, substantially no quantity of magnetically responsive beads 220 bridges a splitting zone 512 during the droplet splitting operation, as shown in FIG. 5A, and substantially no loss of beads occurs, FIG. 5B shows droplet 218 that contains substantially all magnetically responsive beads 220. In other words, the end result of a splitting operation that takes place substantially outside of the magnet forces is that there is substantially no loss of magnetically responsive beads 220 because substantially all of magnetically responsive beads 220 are suitably attracted, immobilize, and retained at a centralized location within the fluid.

Figure 6:
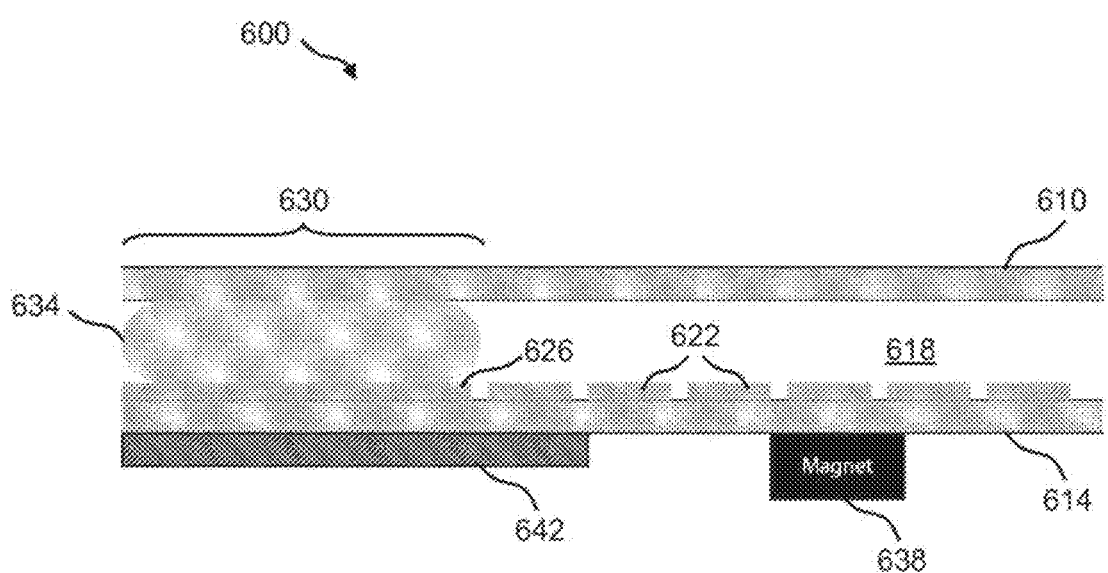
FIG. 6 illustrates a side view of a section of a droplet actuator that includes a magnetic shield for reducing the crossover of magnetic fields.

8.3 Droplet Actuator Configurations with Magnets 8.3.1 Droplet Actuator with Magnetic Shield FIG. 6 illustrates a side view of a droplet actuator 600 that includes a magnetic shield for reducing the crossover of magnetic fields. Droplet actuator 600 includes a top plate 610 and a bottom plate 614 that are arranged having a gap 618 therebetween. An arrangement of electrodes 622, e.g., electrowetting electrodes, may be associated with bottom plate 614 for performing droplet operations and an electrode, such as reservoir electrode 626 that is associated with a fluid reservoir 630 that contains a quantity of fluid 634. One or more droplets (not shown) may be dispensed from the quantity of fluid 634 of reservoir 630 for manipulation along electrodes 622. Additionally, fluid 63 and any droplets dispensed therefrom may optionally contain beads (not shown), which may, in some cases, be magnetically responsive.

Droplet actuator 600 further includes a magnet 638 that is arranged in proximity to the one or more electrodes 622. Magnet 638 may be arranged in sufficient proximity to electrodes 622 in order to permit immobilization of magnetically responsive beads (not shown), e.g., in a droplet positioned on an electrode. In one example, the purpose of magnet 638 is to magnetically immobilize and retain magnetically responsive beads during a droplet splitting operation, e.g., a splitting operation that may be performed in a process for washing magnetically responsive beads.

Additionally, droplet actuator 600 includes a magnetic shield 642 that is arranged in sufficient proximity to fluid reservoir 630 to shield the contents thereof from nearby magnetic fields, such as the magnetic field of magnet 638. Magnetic shield 642 may, for example, be formed of Mu-metal that has sufficiently high magnetic permeability and that is suitable to reduce, preferably substantially eliminate, unwanted magnetic fields from the magnet within fluid reservoir 630. In one example, magnetic shield 642 may be formed of Mu-metal that is supplied by McMaster-Carr (Elmhurst, Ill.). Other examples of magnetic shield 642 materials include Permalloy, iron, steel and nickel.

Droplet actuator 600 is not limited to one magnetic shield and one magnet only, any number of magnetic shields and magnets may be installed therein. Therefore, by use of one or more magnetic shields, the exposure of magnetic beads (not shown) within droplets to magnetic fields may be limited to desired regions only of droplet actuator 600. Magnetic shields may be included on any surface of the droplet actuator and in any arrangement which facilitates suitable shielding.

In one example application, a droplet actuator may be employed to perform multiple assays in parallel and, consequently, there may be a need for generally simultaneous washing of the various magnetic beads that may be manipulated within multiple lanes of electrodes. Without magnetic shields, a wash operation or assay that is performed at a certain location using an associated magnet may be affected by the magnetic field of a distant magnet (i.e., crossover of magnetic fields). By contrast, crossover of magnetic fields between any two magnets may be reduced, preferably substantially eliminated, via the strategic placement of one or mare magnetic shields, such as magnetic shield 642, within the droplet actuator.

8.3.2 Droplet Actuator with Alternating Magnet Configuration

Figure 7:
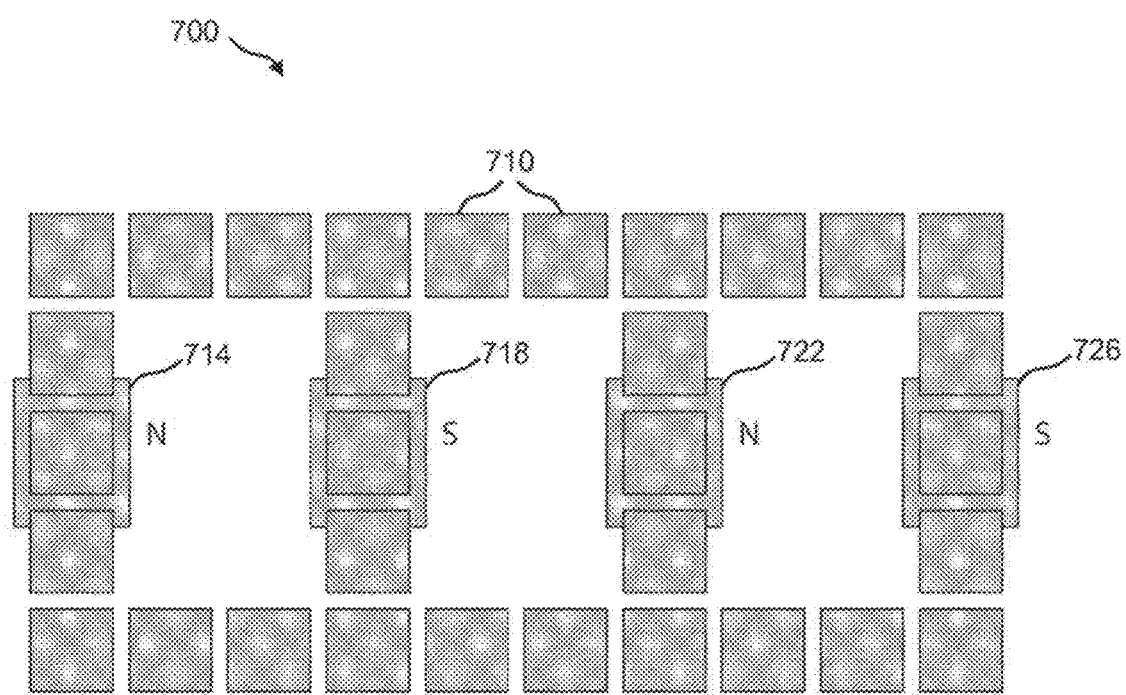
FIG. 7 illustrates a top view of a section of a droplet actuator that includes a magnet having poles that are oppositely arranged for reducing the crossover of magnetic fields.

FIG. 7 illustrates a top view of a droplet actuator 700 that includes a magnet whose poles are oppositely arranged for reducing the crossover of magnetic fields. Droplet actuator 700 includes an arrangement of electrodes 710, e.g., electrowetting electrodes, for performing droplet operations on one or more droplets (not shown). Additionally, a magnet 714 is arranged in close proximity to a first lane of electrodes 710, a magnet 718 is arranged in close proximity to a second lane of electrodes 710, a magnet 722 is arranged in close proximity to a third lane of electrodes 710, and a magnet 726 is arranged in close proximity to a fourth lane of electrodes 710. Magnets 714, 718, 722, and 726 may be arranged in sufficient proximity in electrodes 710 in order to permit immobilization of magnetically responsive beads (trot shown) within one or more droplets (not shown) located on one or more of the electrodes.

In order to reduce, preferably substantially eliminate, crossover of magnetic fields between adjacent magnets, the poles of adjacent magnets are oppositely arranged, which causes the adjacent magnetic fields to cancel. For example and referring again to FIG. 7, the north pole of magnet 722 is oriented upward, and the south pole of magnet 726 is oriented upward. In this way, the magnetic fields are cancelled and the crossover of magnetic fields between magnets 714, 718, 722, and 726 may be reduced, preferably substantially eliminated.

Figure 8:
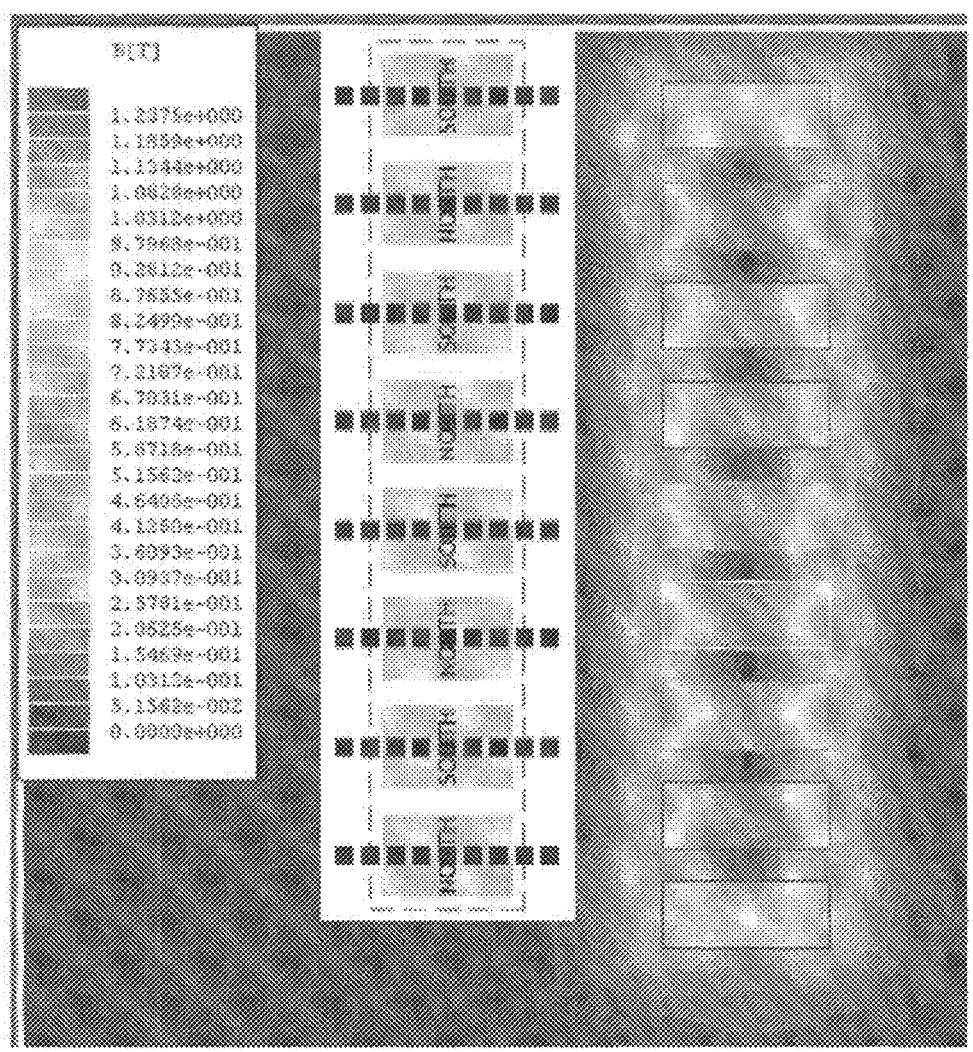
FIG. 8 illustrates a map of magnetic fields that are arranged in a relationship such as the one shown in FIG. 7.

FIG. 8 illustrates a map 800 of magnetic fields arranged in a relationship such as the one shown in FIG. 7.

8.4 Other Techniques

The invention also provides techniques for reducing carryover in a droplet actuator, as well as techniques for improving detection operations.

8.4.1 Technique for Reducing Carryover in a Droplet Actuator

Figure 9:
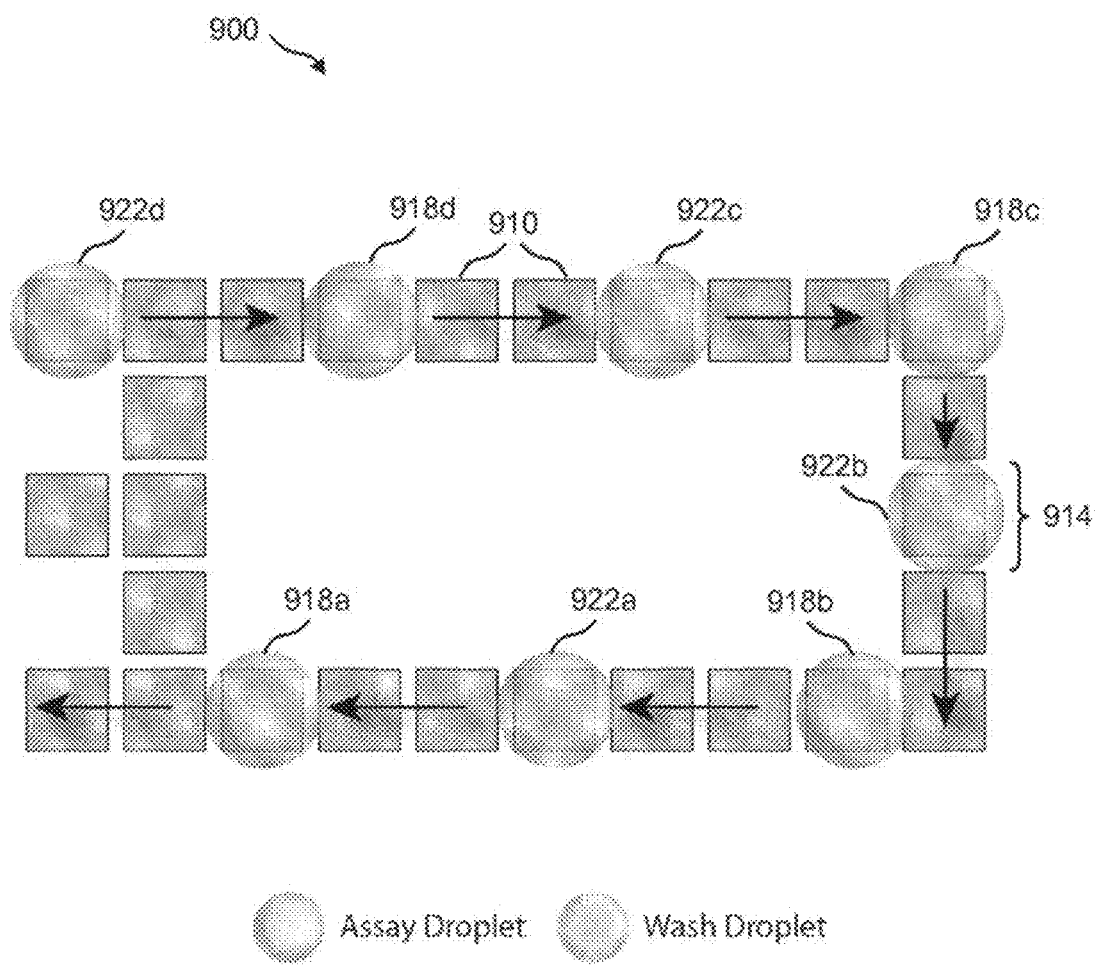
FIG. 9 illustrates a top view of a section of a droplet actuator arranged to reduce carryover at a droplet detection region.

FIG. 9 illustrates a top view of a droplet actuator 900 by which an operation to reduce carryover at a droplet detection region may be performed. Droplet actuator 900 includes an arrangement of electrodes 910, e.g., electrowetting electrodes, for subjecting droplets to droplet operations. Additionally, droplet actuator 900 includes a designated detection region 914 at, for example, a certain electrode 910. Detection region 914 is used to detect droplets positioned thereon or passing therethrough during droplet operations. In one example, droplet detection is performed using a photomultiplier tube (PMT) or photon-counting PMT that is associated with detection region 914. A PMT (not shown) is used to measure light (i.e., detect photons) emitted from a droplet (e.g., due to fluorescence and/or chemiluminescence) when at the electrode that is associated with detection region 914.

In some cases, a build up of substances at a detection region, such as detection region 914, may occur due to carryover, which involves beads or other substances being left behind on surfaces and/or in filler fluid during droplet operations. Carryover may interfere with accurate detection of signals from subsequent droplets and/or interfere with droplet operations by affected electrodes.

Referring again to FIG. 9, a droplet sequencing operation of the invention reduces, preferably substantially eliminates, carryover at detection region 914 by providing a series of alternating assay droplets 918 and wash droplets 922. In one example, an assay droplet 918a passes through detection region 914, followed by a wash droplet 922a, followed by an assay droplet 918b, followed by a wash droplet 922b, followed by an assay droplet 918c, followed by a wash droplet 922c, followed by an assay droplet 918d, which is followed by a wash droplet 922d. As assay droplets 918a, 918b, 918c, and 918d have the potential to degrade the function of detection region 914 due to crossover, wash droplets 922a, 922b, 922c, and 922d perform a cleaning operation of the surfaces that are associated with detection region 914. The cleaning process of the invention is not limited to the sequence that is shown in FIG. 9. Any sequence is possible as long as the sequence includes a suitable number of wash droplets to order to suitably clean the detection region. For example, depending on the requirements of the specific assay, multiple wash droplets may be provided between assay droplets and/or multiple assay droplets may be provided between wash droplets, e.g., AAWAAWAAW, AAAWAAAWAAAW, AWWAWWAWW, AWWWAWWWAWWW, AAWWAAWWAAWW, AAAWWWAAAWWWAAAWWW, etc., where A=assay droplet and W=wash droplet. It should be noted that it is not necessary for assay and wash droplets to be the same size. Assay droplets may be larger or wash droplets may be larger. The larger droplet may be subjected to droplet operations as a slug (e.g., a slug occupying 4 electrodes) or as a single large droplet (e.g. a 4× droplet occupying as many electrodes as it naturally covers without being formed into a slug). Each arrangement may result in a different cleaning result. It is also not necessary for the assay droplets and wash droplets to follow the same path. For example, their paths may intersect at the location needing to be cleaned.

FIGS. 10A and 10B illustrate a top view of a droplet actuator 1000 by which another operation for reducing carryover may be performed. Droplet actuator 1000 includes an arrangement of electrodes 1010, e.g., electrowetting electrodes, for performing droplet operations on one or more droplets, such as assay droplets 1014 and 1018 (FIG. 10A) and wash droplet 1022 (FIG. 10B). Additionally, a magnet 1026 is arranged in close proximity to a certain electrode 1010. Magnet 1026 may be arranged in sufficient proximity to the certain electrode 1010 in order to permit immobilization of magnetically responsive beads within one or more droplets, such as magnetic beads 1030 within assay droplet 1014.

During, for example, a droplet split operation, a quantity of "satellite" droplets may be left behind at the point at which the split occurs. For example and referring to FIG. 10A, a droplet split operation by which assay droplet 1014 is formed by splitting from assay droplet 1018 may result in a certain quantity of satellite droplets 1034 being left behind upon a certain electrode 1010. Satellite droplets, such as satellite droplets 1034, may be the source of carryover (cross contamination) from one droplet to another, which is not desired. FIG. 10B illustrates that a wash droplet, such as wash droplet 1022, may be transported along electrodes 1010 subsequent to the assay operations of, for example, assay droplets 1018 and 1014 in order to capture satellite droplets 1034 and transport them away prior the next assay operation occurs. In this way, electrodes 1010 are cleaned between assay operations. The cleaning process of the invention is not limited to the sequence that is shown in FIGS. 10A and 10B. Any sequence is possible as long the sequence includes a suitable number of wash droplets in order to suitably clean the electrodes.

8.4.2 Improving Detection Operations in a Droplet Actuator

Figure 11:
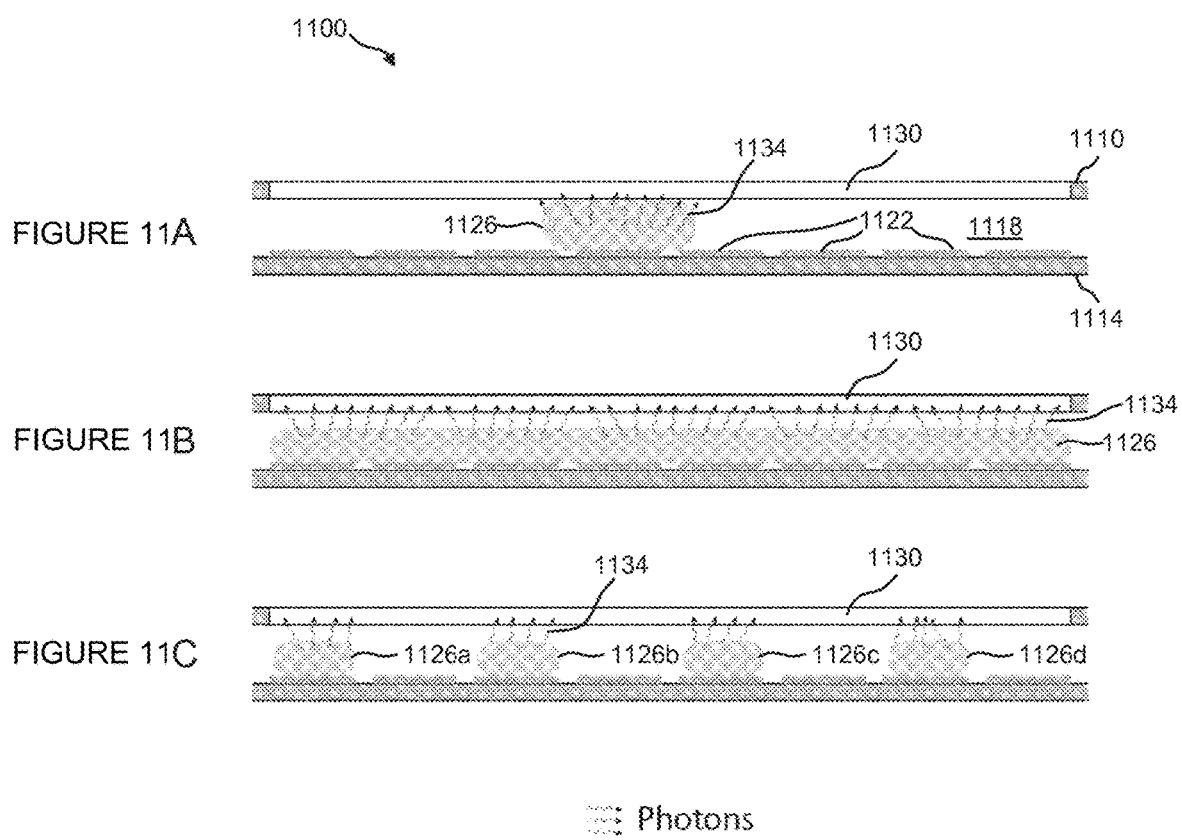
FIGS. 11A, 11B, and 11C illustrate side views of section of a droplet actuator configured for improving the sensitivity of droplet detection.

FIGS. 11A, 11B, and 11C illustrate side views of droplet actuator 1100 by which respective operations for improving the sensitivity of droplet detection may be performed. Droplet actuator 1100 includes a top plate 1110 and a bottom plate 1114 that are arranged having a gap 1118 therebetween. An arrangement of electrodes 1122, e.g., electrowetting electrodes, may be associated with bottom plate 1114 for performing droplet operations on a droplet 1126. A PMT window 1130 may be associated with top plate 1110, by which a PMT (not shown) is used to measure light (i.e., detect photons 1134) emitted from droplet 1126.

FIG. 11A shows a method of improving the sensitivity of droplet detection by spreading out a droplet, such as droplet 1126, in order to increase the surface area that is exposed to PMT window 1130 and, thus, increase the number of photons 1134 that may be detected. A droplet may be spread linearly across one or more electrodes 1122 depending on the volume of the droplet. In the case of a small-volume droplet, a buffer droplet may be added to make the droplet larger, as long as losses due to dilution by the buffer droplet are offset by the increased droplet area exposed to the PMT. For example, FIG. 11B shows droplet 1126 that is spread continuously across multiple electrodes 1122, which increases the number of photons 1134 that may reach PMT window 130 and may be detected by the PMT.

FIG. 11C shows a scenario wherein droplet 1126 is split up into multiple droplets 1126, such as droplets 1126a, 1126b, 1126c, and 1126d that are on multiple electrodes 1122. Again, the surface area that is exposed to PMT window 1130 is increased, which increases the number of photons 1134 that may reach PMT window 1130 and may be detected by the PMT. Alternatively and referring again to FIGS. 11A, 11B, 11C, the spreading of a droplet, such as droplet 1126, is not limited to linear spreading only. The droplet may be spread two dimensions, such as across a grid or array or electrodes 1122, in order to increase the surfaced area that is exposed to PMT window 1130. Alternatively, one or more large-area electrodes may be provided, across which one or more droplets may be spread.

Figure 12:
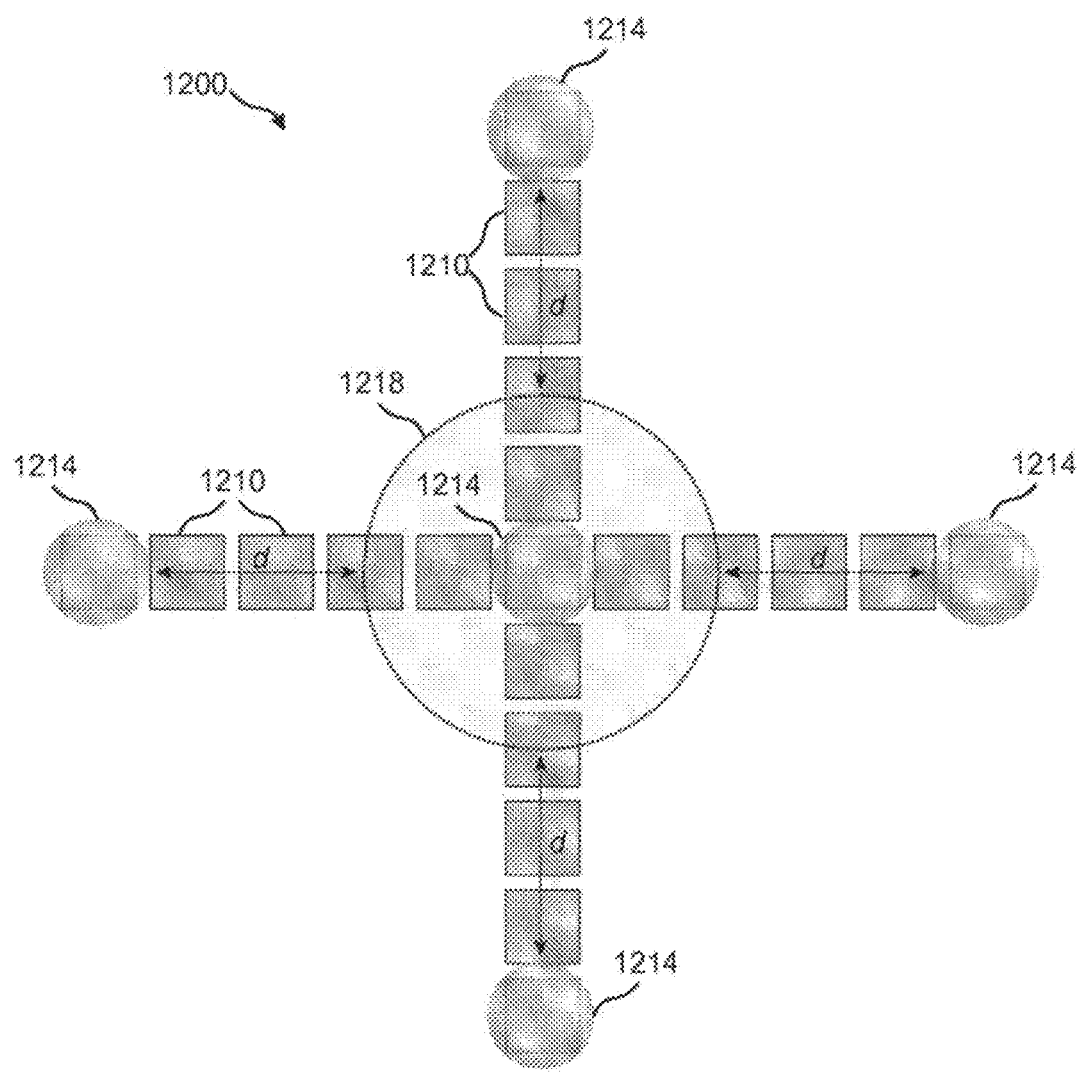
FIG. 12 illustrates a top view of a section of a droplet actuator configured for improving the sensitivity of droplet detection.

FIG. 12 illustrates a top view of a droplet actuator 1200 for improving the sensitivity of droplet detection. Droplet actuator 1200 includes an arrangement of electrodes 1210, e.g., electrowetting electrodes, for performing droplet operations on multiple droplets 1214. Additionally, droplet actuator 1200 may include a droplet detection region 1218 that has an associated PMT (not shown) for measuring light that is emitted from a certain droplet 1214 when present. In order to reduce, preferably substantially eliminate, the carryover of light from a distant droplet 1214 to droplet detection region 1218, a minimum distance d is maintained in all direction between the outer perimeter of droplet detection region 1218 and any distant droplets 1214 within droplet actuator 1200, as shown in FIG. 12. The minimum distance d is sufficiently large to reduce, preferably substantially eliminate, the carryover of light from a distant droplet 1214 to droplet detection region 1218. As a result, in a droplet actuator that includes multiple droplets 1214, a spacing is maintained during detection between the target droplet 1214 that is being measured and a distant droplet 1214, such that the carryover of light from the distant droplet 1214 to droplet detection region 1218 is reduced, preferably substantially eliminated. As a specific case the distance d is an integer multiple m of a unit electrode size, and the droplet detection may be conducted on a set of electrodes which are electrically connected as an m phased bus. Alternatively, FIG. 13 (described below) describes a scenario wherein the real-estate with a droplet actuator is limited and, therefore, sufficient spacings between droplets, as described in FIG. 12, may not be achieved.

In an alternative embodiment, cross-over from nearby droplets is eliminated by using optical elements, such as one or more lenses, which focus only light from the droplet being interrogated onto the sensor and eliminates signal from other droplets.

Figure 13:
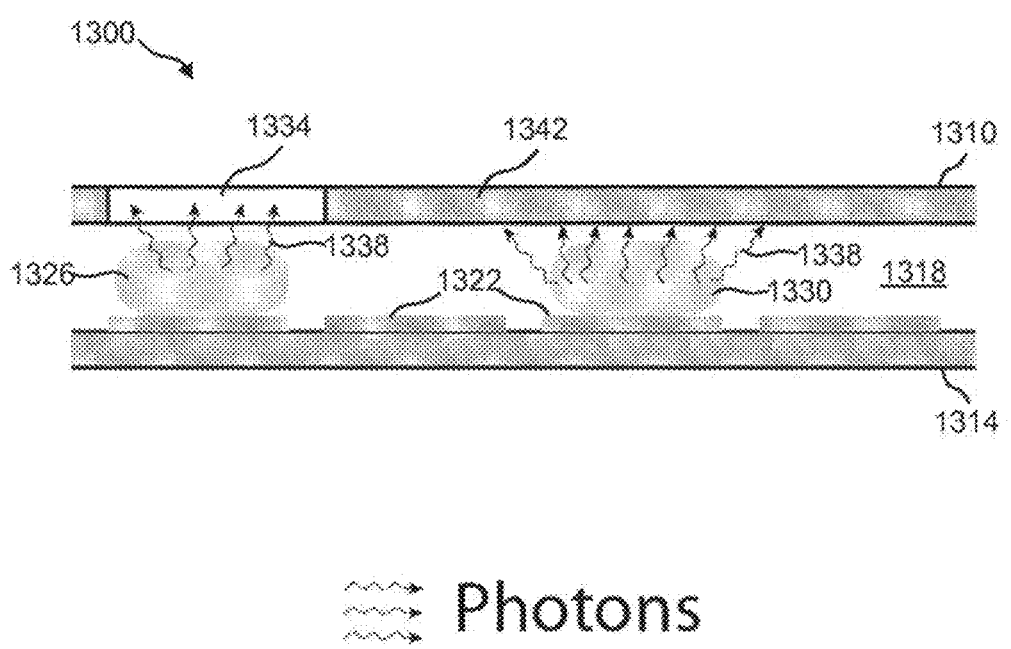
FIG. 13 illustrates a side view of a section of a droplet actuator configured for improving the sensitivity of droplet detection.

FIG. 13 illustrates a side view of a droplet actuator 1300 for improving the sensitivity of droplet detection. Droplet actuator 1300 includes a top plate 1310 and a bottom plate 1314 that are arranged having a gap 1318 therebetween. An arrangement of electrodes 1322, e.g., electrowetting electrodes, may be associated with bottom plate 1314 for performing droplet operations on droplets, such as a droplet 1326 and a droplet 1330. A PMT window 1334 may be associated with top plate 1310, by which a PMT (not shown) is used to measure light (i.e., detect photons 1338) that is emitted from, for example, droplet 1326. Because the spacing between, for example, droplet 1326 at PMT window 1334 and distant droplet 1330 is not suitably sufficient to avoid the carryover of light from droplet 1330 to PMT window 1334, a mask 1342 is provided upon top plate 1310. The purpose of mask 1342 is to block light from a distant droplet from carrying over to PMT window 1334, which is the detection region of a target droplet.

Mask 1342 may be formed upon top plate 1310 via a layer of any light-absorbing material, as long as the material that is used is compatible with the electrowetting process and does not unduly interfere with the droplet actuator operations. In one example, mask 1342 may be formed by applying a layer of black paint to top plate 1310, such that one or more windows, such as PMT window 1334, are provided in selected defection regions of droplet actuator 1300. In the example shown in FIG. 13, mask 1342 reduces, preferably substantially eliminates, the carry over of light from distant droplet 1330 to the target droplet 1320 at PMT window 1334. In another example the mask 1342 is formed by an opaque conductor on the side of the top plated 1310 facing the droplet. The conductor may, for example, be aluminum, chromium, copper, or platinum. The conductor may additionally serve as an electrical reference electrode.

8.8 Droplet Actuators with Magnet Assemblies

Figure 14A:
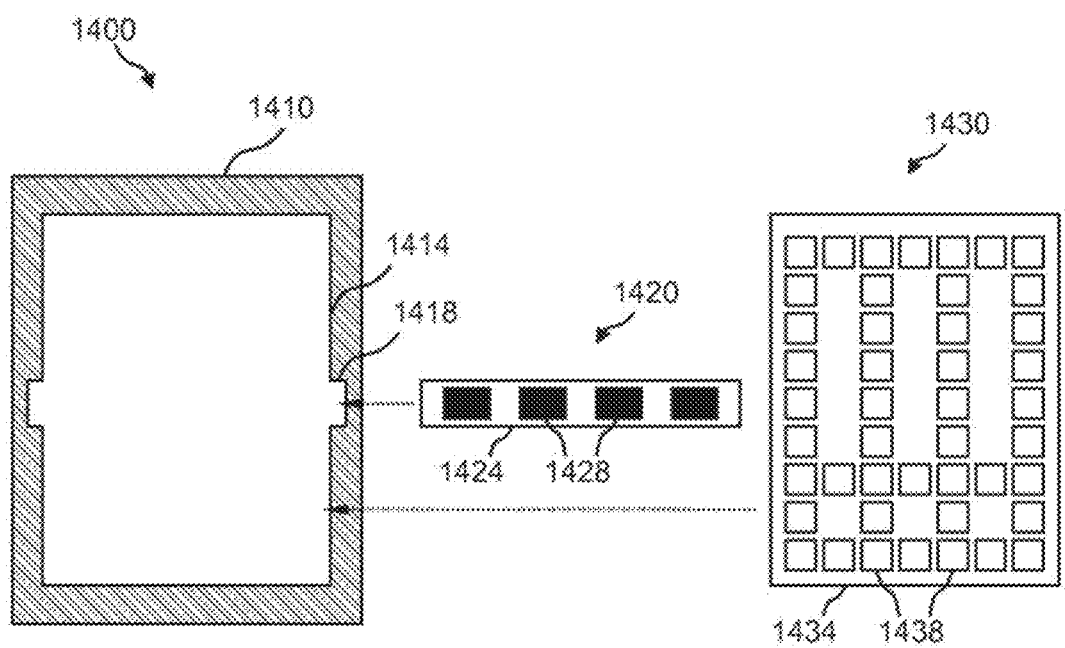
FIGS. 14A and 14B illustrate top views of a modular droplet actuator assembly, which provides a universal assembly for orienting a magnet assembly to a droplet actuator.
Figure 14B:
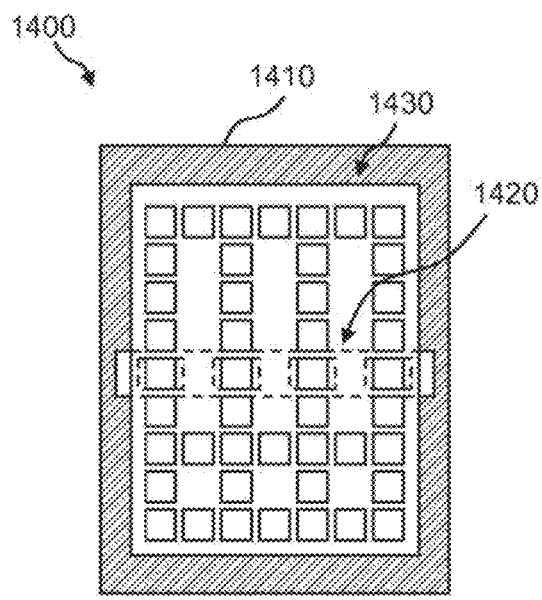

FIGS. 14A and 14B illustrate top views of a modular droplet actuator assembly 1400, which is a nonlimiting example of a universal assembly for orienting a magnet assembly to a droplet actuator. Modular droplet actuator assembly 1400 include, for example, a mount 1410, a magnet assembly 1420, and a droplet actuator 1430, FIG. 14A shows modular droplet actuate assembly 1400 when disassembled. FIG. 14B shows modular droplet actuator assembly 1400 when assembled.

Magnet assembly 1420 may include a substrate 1424 upon which is mounted one or more magnets 1428, as shown in FIG. 14A. The magnets 1428 may be permanently affixed to substrate 1424 or may be removable. Removable magnets 1428 facilitate selection by a user of magnets having desired properties, such as desired magnet strength. In one embodiment, a droplet actuator instrument is provided with a droplet actuator assembly 1400 including a mount 1410 and a magnet assembly 1420 without magnets. In another embodiment, the user is also provided with magnets having specified properties which may be affixed by the user to the magnet assembly 1420. In another embodiment, the user is also provided with sets of magnets having various specified characteristics such that the user may select a set of one or more magnets having desired properties and affix the selected set to the magnet assembly 1420.

Magnets may be marked or coded (e.g., color coded) to facilitate selection of magnets having appropriate properties, as well as marked to show the orientation of the magnet's magnetic field (e.g., by color coding or otherwise marking the North and South faces of the magnets). Similarly, the magnet assembly 1420 may be marked to show the desired orientation of magnets inserted therein, and in some embodiments, magnets may be shaped to permit them to be affixed to the magnet assembly 1420 only in an appropriate orientation.

Moreover, in another embodiment, the user may be provided with magnet assemblies 1420 having magnets already affixed thereto, wherein the magnet assemblies 1420 each have different magnet configurations, e.g., sets of magnets having different properties. The user may select the magnet configuration having magnets having properties appropriate to the user's desired use for the instrument. Magnet assembly 1420 may be marked or otherwise color coded to facilitate selection by the user. Magnet properties may, for example, be selected based on the properties of beads selected by the user.

Droplet actuator 1430 may include a substrate 1434 upon which is an arrangement of electrodes 1438, e.g., electrowetting electrodes, as shown in FIG. 14A. A second (top) substrate may also be included (not shown).

Magnet assembly 1420 is designed such that magnets 1428 substantially align with certain electrodes 1438 of interest on droplet actuator 1430. For example, in some embodiments, parallel configurations of magnets may be present for conducting parallel assay steps on droplet actuator 1430. Magnets may be configured and oriented, for example, according to the various configurations and orientations described herein.

Mount 1410 may serve as a universal platform for mounting a magnet assembly, such as magnet assembly 1420, and a droplet actuator, such as droplet actuator 1430. In one embodiment, mount 1410 is configured to accept a wide variety of magnet assemblies 1420 and a wide variety of droplet actuators 1430. Magnet assembly 1420 may include one or more magnets arranged in any of a variety of patterns and employing any of a variety of magnet properties. FIG. 14 illustrates a row of magnets, but magnets may also be provided in a grid or any arrangement that places the magnets in their proper position in relation to the droplet actuator 1430 in order to facilitate desired operations on the droplet actuator.

In one example, magnet assembly 1420 and droplet actuator 1430 may be installed into mount 1410 via respective fittings 1418 and 1414. Fittings may, for example, involve slots into which the mount 1410 may be fitted, openings on the mount 1410 for accepting posts on the magnet assemblies 1420 or vice versa, openings on the mount 1410 for accepting screws on the magnet assemblies 1420, threaded posts for accepting bolts, various spring loaded mechanisms, recessed trays, complimentary fittings, and the like. Any mechanism which facilitates sufficiently secure attachment to permit the device to function for its intended purpose will suffice.

Further, the mount 1410 may include multiple fittings for multiple possible positions of magnet assembly 1420 and/or droplet actuator 1430, and/or mounting of multiple magnet assemblies 1420 and/or multiple droplet actuators 1430 in a single mount 1410. Further, mount 1410 may be configured to permit magnet assemblies 1420 to be mounted above, below and/or beside the droplet actuator 1430, i.e., in any relationship with the droplet actuator. With droplet actuator 1430 installed in modular mount 1410, any magnet assembly of interest, such as magnet assembly 1420, may be inserted into modular droplet actuator assembly 1400 via, for example, the slot.

Figure 15:
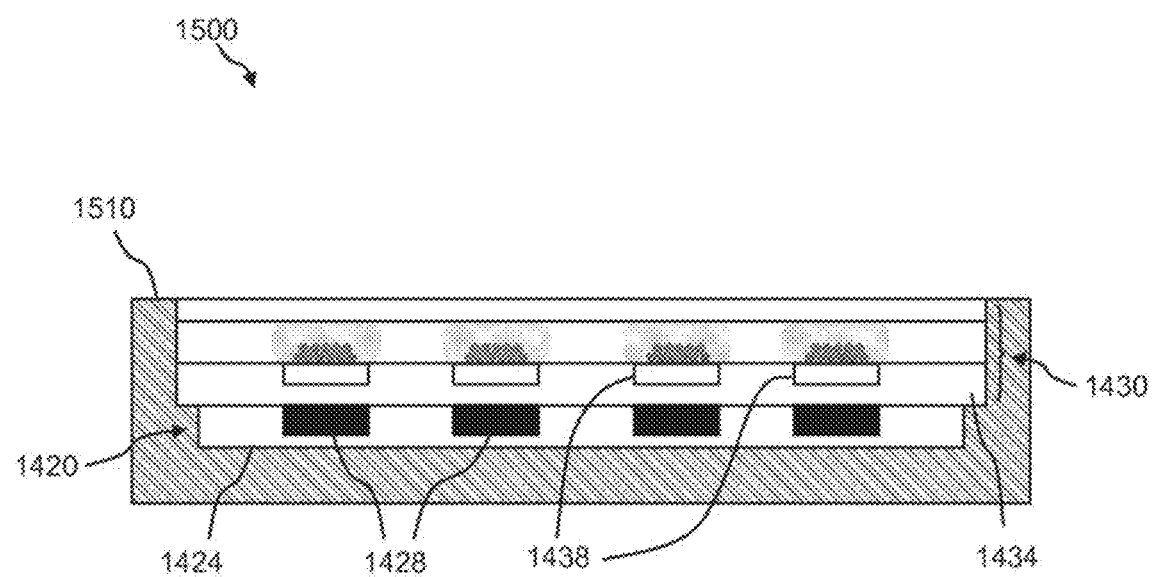
FIG. 15 illustrates a side view of a modular droplet actuator assembly, which is another nonlimiting example of a universal assembly for orienting a magnet assembly to a droplet actuator.

FIG. 15 illustrates a side view of a modular droplet actuator assembly 1500, which is another nonlimiting example of a universal assembly for orienting a magnet assembly to a droplet actuator, similar to the assembly 1400 shown in FIG. 14, except that mount 1410 is replaced with a mount 1510. Mount 1510 includes recessed trays into which magnet assembly 1420 and droplet actuator 1430 may be fitted in order to provide a "drop in" method of loading.

Referring to FIGS. 14A, 14B, and 15, an aspect of the invention is that the slots or other attachment means serve to orient the magnet substrate and the droplet actuator so as to align the magnets on the magnet assembly with the appropriate electrodes or electrode paths on the droplet actuator. In this manner, the magnets may be removed when not needed for an assay. Additionally, different magnet mounts with different distributions of magnets may be provided for different types of assays or different droplet actuator layouts.

8.6 Magnets

In addition to other aspects already described, it should be noted that magnets selected for use with the invention may be permanent or electromagnets. There may be a relationship between the magnetically responsive content of the beads at the droplet and the magnetic strength/pull force. Therefore, the magnet strength/pull force of the magnet may be selected relative to the responsiveness of the magnet beads such that it is:

sufficiently strong relative to the magnetic responsiveness of the bends to substantially immobilize magnetically responsive beads;

not so strong relative to the magnetic responsiveness of the beads that it significantly magnetizes the beads and, thus, causes irreversible formation of clumps of beads;

not so strong relative to the magnetic responsiveness of the beads that resuspension occurs poorly when the magnet field is removed; and/or not so strong relative to the magnetic responsiveness of the beads that the beads are pulled out of the droplet altogether.

In some embodiments, the magnet may have high magnetic strength (in Tesla) with lesser pull force (in pounds). In one example, magnet is a neodymium permanent magnet that has a surface field strength of about 1 Tesla (T). In another example, the magnet is an electromagnet that has a surface field strength of about 1 T, which may be turned on and off electronically. Where a permanent magnet is used, the magnet may be moved away from the magnetically responsive bead-containing droplet for uses in which it is desirable to remove the influence of the magnetic field. While not limited to the following ranges, it is understood that ranges of magnetic strength that generally encompasses the useful strength of the present invention can include: a broad range of 0.01 T to 100 T (pulsed) or 45 T (continuous); an intermediate range of 0.01 T to 10 T: and a narrow range of 0.1 T to 1 T (preferably 0.5 T).

8.7 Droplet Composition

Droplets including magnetic beads and subjected to droplet splitting operations may include any of a wide variety of samples, reagents, and buffers useful for conducting assays using the beads. For example, during washing, the droplet may include a buffer, such as a phosphate-buffered saline (PBS) buffer with a surfactant that is suitable for use in magnetic based immunoassays. Preferred surfactants are these which facilitate immobilization and/or resuspension of beads following immobilization by magnetic forces. The surfactant and amount of surfactant may be adjusted to provide a substantial improvement in suspension as compared to a control solution lacking the surfactant. In one embodiment, the droplet includes PBS buffer with about 0.01% Tween® 20.

A hydrophilic polymer and/or surfactant may be included in the droplet to facilitate retention and resuspension of magnetically responsive beads during splitting operation. The droplet may include a wide variety of liquids immiscible with the filler fluid. Examples of buffers include, but are not limited to, phosphate-buffered saline (PBS) buffer and Tris buffer saline. In one embodiment, the droplet fluid includes a buffer, such as the PBS buffet; and any surfactant that is suitable for use in magnetic based immunoassays.

Preferred hydrophilic polymers and surfactants are those which facilitate resuspension of beads following immobilization by magnetic forces. The surfactant and amount of surfactant may be adjusted to provide a substantial improvement in resuspension as compared to a control solution lacking the surfactant. Examples of surfactants that are suitable for use in magnetic based immunoassays include, but are not limited to, polysorbate 20, which is commercially known as Tween®20, and Triton X-100, Tween® 20 may be supplied by, for example, Pierce Biotechnology, Inc. (Woburn, Mass.). Triton® X-100 may be supplied by, for example, Rohm & Haas Co (Philadelphia, Pa.). In one example, the droplet fluid within the droplet actuator is a mix of PBS with Tween® 20 in the range of from about 0.001% to about 0.1%. In another example, the droplet fluid within the droplet actuator is a mix of PBS with about 0.01% Tween® 20.

Other examples include pluronic surfactants, polyethylene glycol (PEG), methoxypolethylene glycol (MPEG), poly-sorbate (polyoxyethylene sorbitan monoclcates or Tween®), polyoxyethylene octyl phenyl ether (Triton X-100®), polyvinyl pyrollidone, polyacrylic acid (and crosslinked polyacrylic acid such as carbomer), polyglycosides (nonionic glycosidic surfactants such as octyl glucopyranoside) and soluble polysaccharides (and derivatives thereof) such as heparin, dextrans, methyl cellulose, propyl methyl cellulose (and other cellulose esters and ethers), dextrins, maltodextrins, glactomannans, arbainoglactans, beta glucans, alginates, agar, carrageenan, and plant gums such as xanthan gum, psyllium, guar gum, gum traganth, gun karya, gum ghatti and gum acacia. The particular additive can be selected for maximum compatibility with a specific microfluidic sample.

8.8 Droplet Actuator

For examples of droplet actuator architectures that are suitable for use with the present invention, see U.S. Pat. No. 6,911,132, entitled, "Apparatus for Manipulating Droplets by Electrowetting-Based Techniques," issued on Jun. 28, 2005, to Pamula et al.; U.S. patent application Ser. No. 11/343,284, entitled, "Apparatuses and methods for Manipulating Droplets on a Printed Circuit Board," filed on filed on Jan. 30, 2006; U.S. Pat. No. 6,773,566, entitled, "Electrostatic Actuators for Microfluidics and Methods for Using Same," issued on Aug. 10, 2004 and U.S. Pat. No. 6,565,727, entitled, "Actuators for Microfluidics Without Moving Parts," issued on Jan. 24, 2000, both to Shenderov et al., and International Patent Application No. PCT/US 06/47486 to Pollack et al., entitled, "Droplet-Based Biochemistry," filed on Dec. 11, 2006, the disclosures of which are incorporated herein by reference. Droplet actuator techniques for immobilizing magnetic beads and/or non-magnetic beads are described in the foregoing international patent applications and in Sista, et al., U.S. Patent Application No. 60/900,653, filed on Feb. 9, 2007, entitled "Immobilization of magnetically-responsive beads during droplet operations": Sista et al., U.S. Patent Application No. 60/969, 736, filed on Sep. 4, 2007, entitled "Droplet Actuator Assay Improvements"; and Allen et al., U.S. Patent Application No. 60/957,717, filed on Aug. 24, 2007, entitled "Bead washing using physical barriers," the entire disclosures of which is incorporated herein by reference. Combinations of these various techniques are within the scope of this invention.

8.9 Fluids

For examples of fluids that may be subjected to droplet operations of the invention, see the patents listed in section 8.8, especially International Patent Application No. PCT/US 06/47486, entitled, "Droplet-Based Biochemistry," filed on Dec. 11, 2006. In some embodiments, the droplet is a sample fluid, such as a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transodates, exudates, cystic fluid, bile, urine, gastric fluid, intestinal fluid, fecal samples, fluidized tissues, fluidized organisms, biological swabs and biological washes. In some embodiments, the fluid that is loaded includes a reagent, such as water, deionized water, saline solutions, acidic solutions, basic solutions, detergent solutions and/or buffers. In some embodiments, the fluid that is loaded includes a reagent, such as a reagent for a biochemical protocol, such as a nucleic acid amplification protocol, an affinity-based assay protocol, a sequencing protocol, and/or a protocol for analyses of biological fluids.

8.10 Filler Fluids

As noted, the gap is typically filled with a filler fluid. The filler fluid may, for example, be a low-viscosity oil, such as silicone oil. Other examples, of filler fluids are provided in International Patent Application No. PCT/US 06/47486, entitled, "Droplet-Based Biochemistry," filed on Dec. 11, 2006.

8.11 Washing Magnetically Responsive Beads

For protocols making use of beads, droplets with beads can be combined using droplet operations with one or more wash droplets. Then, while retaining the beads (e.g., physically or magnetically) using magnet configurations of the invention, the merged droplet may be divided using droplet operations into two or more droplets: one or more droplets with beads and one or more droplets without a substantial amount of beads. In one embodiment, the merged droplet is divided using droplet operations into one droplet with beads and one droplet without a substantial amount of beads.

Generally, each execution of a washing protocol results in retention of sufficient beads for conducting the intended assay without unduly detrimental effects on the results of the assay. In certain embodiments, each division of the merged droplet results in retention of more than 90, 95, 97, 98, 99, 99.1, 99.2, 99.3, 99.4, 99.5, 99.6, 99.7, 99.8, 99, 99.9, 99.99, 99.999, 99.9999, 99.99999, or 99.999999 percent of beads. In other embodiments, each execution of a washing protocol to achieve a predetermined reduction in the concentration and/or amount of removed substance results in retention of more than 99, 99.1, 99.2, 99.3, 99.4, 99.5, 99.6, 99.7, 99.8, 99, 99.9, 99.99, 99.999, 99.9999, 99.99999, or 99.999999 percent of beads. In still other embodiments, the amount of retained beads is calculated and the results are adjusted accordingly.

In some embodiments, beads can be washed in reservoirs in which the bead-containing droplet and wash droplets are combined, beads are retained (for example by a magnet, by physical structures, electrostatic forces), and droplets lacking beads are dispensed from the reservoir using droplet operations. For example, beads can be washed by dilute-and-dispense strategy whereby a wash buffer is added to the reservoir to dilute the contents, magnetically responsive beads are localized within the reservoir with a magnet and moist of the solution is dispensed front the reservoir, and this cycle is repeated till acceptable levels of washing are achieved.

As an example, washing magnetically responsive beads may generally include the following steps:

(1) providing a droplet comprising magnetically responsive beads and unbound substances in proximity with a magnet;
(2) using droplet operations to combine a wash droplet with the droplet comprising the magnetically responsive beads;
(3) immobilizing the beads by application of a magnetic field;
(4) using droplet operations to remove some or all of the droplet surrounding the beads to yield a droplet comprising the beads with a reduced concentration of unbound components and a droplet comprising unbound components;
(5) releasing the beads by removing the magnetic field; and
(6) repeating steps (2) to (3) or (2) to (4) until a predetermined degree of purification is achieved.

In this manner, unbound substances, such as contaminants, byproducts or excess reagents, can be separated from the beads. Each cycle produces a droplet including the beads but with a decreased level of the unwanted substances. Step (5) is not required in each washing cycle; however, it may be useful to enhance washing by freeing contaminants which may be trapped in the immobilized beads. Steps may be performed in a different order, e.g., steps (2) and (3) may be reversed. Steps in the washing protocol may be accomplished on a droplet actuator using droplet operations as described herein.

In embodiments in which magnetically responsive beads are used, the inventors have found that application of a magnetic field though useful for temporarily immobilizing beads, moving beads and/or positioning beads, sometimes results in unwanted aggregation of the beads. As already noted, in one embodiment, a hydrophilic polymer and/or surfactant is included to prevent or reduce bead aggregation.

Hydrophilic polymers and surfactants should be selected and used in amounts which reduce or eliminate bead aggregation and minimize non-specific absorption while at the same time not resulting is significant loss of target analytes or reagents from the droplet. In one embodiment, the hydrophilic polymer and/or surfactant reduces bead clumping in a droplet in a non-gaseous filler fluid and specifically does not serve to reduce molecular adsorption of droplet components to a surface of the droplet actuator.

Another approach to eliminating or reducing clumping aggregation of beads involves the use of smaller numbers of larger beads. Any number of beads which can be contained in a droplet during one or more droplet operations may be used. In some embodiments, the number of magnetically responsible beads can range from 1 to several 100,000's. For example, in one embodiment, the invention makes use of one to 100 magnetically responsible beads per droplet. For example, the invention may make use of 1, 2, 3, 4, 5, 6, 7, 8, 9, 10 . . . 100 magnetically responsive beads per droplet. In one embodiment, the number of magnetically responsive beads is from one to 10. Use of smaller numbers of magnetically responsive beads permits larger beads to be used. For example, in one embodiment, the invention makes use of one to 100 magnetically responsive beads per droplet, where the beads have an average diameter of about 25 to about 100 microns. In another embodiment the invention makes use of one to 10 magnetically responsive beads per droplet, where the beads have an average diameter of about 50 to about 100 microns.

CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A modular droplet actuator assembly, comprising:
   a. a first module comprising a droplet actuator comprising a first droplet actuator substrate, the first droplet actuator substrate having an arrangement of electrodes thereon and the arrangement of electrodes configured to conduct one or more droplet operations;
   b. a second module comprising one or more magnets and a magnet assembly comprising a first magnet assembly substrate that is not a top plate of the droplet actuator, wherein the first magnet assembly substrate has one or more magnets mounted thereon to form a populated magnet assembly; and
   c. a third module comprising a mount configured for mounting the magnet assembly and droplet actuator thereto, the mount having first and second recessed trays to receive the magnet assembly and droplet actuator, wherein the first recessed tray is positioned below the second recessed tray, such that when the populated magnet assembly and the droplet actuator are mounted in the mount, the one or more magnets of the populated magnet assembly are aligned with one or more predetermined positions on the arrangement of electrodes to magnetically effect droplet operations utilizing magnetically responsive beads at the predetermined positions.

2. The modular droplet actuator assembly of claim 1 wherein magnet assembly and droplet actuator are mounted to the mount such that the magnet assembly is substantially aligned with certain electrodes of the arrangement of electrodes of the droplet actuator.

3. The modular droplet actuator assembly of claim 1 wherein the electrodes comprise electrowetting electrodes.

4. The modular droplet actuator assembly of claim 1 wherein the droplet actuator further comprises a second droplet actuator substrate spaced apart from the first droplet actuator substrate to form a gap therebetween.

5. The modular droplet actuator assembly of claim 1 wherein the one or more magnets are at least one of permanently and removably mounted to the first magnet assembly substrate.

6. The modular droplet actuator assembly of claim 5 wherein the one or more magnets are grouped in one or more sets of magnets based on certain magnetic properties.

7. The modular droplet actuator assembly of claim 6 wherein the magnetic properties comprise one or more of magnetic field orientation and magnetic strength.

8. The modular droplet actuator assembly of claim 6 wherein a user selects a set of the one or more sets of magnets based on desired magnet properties.

9. The modular droplet actuator assembly of claim 5 wherein the one or more magnets are shaped such that they can be mounted to the magnet assembly only in a predefined orientation.

10. The modular droplet actuator assembly of claim 5 wherein the one or more magnets are mounted to the magnet assembly in one of a row and grid arrangement.

11. The modular droplet actuator assembly of claim 5 wherein the one or more magnets and/or magnet assemblies are marked or coded based on their magnetic properties.

12. The modular droplet actuator assembly of claim 1 wherein the magnet assembly and droplet actuator are mounted into the mount via one or more fittings.

13. The modular droplet actuator assembly of claim 12 wherein the one or more fittings comprise one or more slots and/or openings.

14. The modular droplet actuator assembly of claim 12 wherein the one or more fittings comprise one or more of posts, screws, threaded posts, nuts, spring loaded mechanisms, and complimentary fittings.

15. The modular droplet actuator assembly of claim 12 wherein the one or more fittings are configured such that the magnet assembly and/or droplet actuator can be mounted in multiple positions onto the mount.

16. The modular droplet actuator assembly of claim 12 wherein the one or more fittings are configured such that multiple magnet assemblies and/or multiple droplet actuators can be mounted onto the mount.

17. The modular droplet actuator assembly of claim 12 wherein the one or more fittings are configured such that the magnet assembly can be mounted one or more of above, below, and/or beside the droplet actuator.

18. The modular droplet actuator assembly of claim 1 wherein at least one of the one or more magnets is a neodymium permanent magnet.

* * * * *